United States Patent
Fukuda et al.

(10) Patent No.: US 9,217,142 B2
(45) Date of Patent: Dec. 22, 2015

(54) CULTURE METHOD AND CULTURE DEVICE FOR CULTURING CELLS ADHERED ONTO AN ELECTRODE LAYER

(75) Inventors: Junji Fukuda, Yokohama (JP); Hiroaki Suzuki, Ibaraki (JP); Naoto Mochizuki, Ibaraki (JP); Takahiro Kakegawa, Ibaraki (JP)

(73) Assignee: UNIVERSITY OF TSUKUBA, Tsukuba (JP)

( * ) Notice: Subject to any disclaimer, the term of this patent is extended or adjusted under 35 U.S.C. 154(b) by 33 days.

(21) Appl. No.: 13/820,907

(22) PCT Filed: Sep. 8, 2011

(86) PCT No.: PCT/JP2011/070533
§ 371 (c)(1),
(2), (4) Date: Mar. 5, 2013

(87) PCT Pub. No.: WO2012/033181
PCT Pub. Date: Mar. 15, 2012

(65) Prior Publication Data
US 2013/0171712 A1  Jul. 4, 2013

(30) Foreign Application Priority Data
Sep. 10, 2010  (JP) .................................. 2010-203741

(51) Int. Cl.
C12N 11/02 (2006.01)
C12M 1/32 (2006.01)
C12M 1/26 (2006.01)
C12N 5/00 (2006.01)
C12M 1/12 (2006.01)

(52) U.S. Cl.
CPC ............... *C12N 11/02* (2013.01); *C12M 23/12* (2013.01); *C12M 25/08* (2013.01); *C12M 33/00* (2013.01); *C12N 5/0068* (2013.01); *C12N 2509/00* (2013.01); *C12N 2529/00* (2013.01); *C12N 2533/50* (2013.01)

(58) Field of Classification Search
CPC .. C12N 11/02; C12N 5/0068; C12N 2533/50; C12N 2509/00; C12N 2529/00; C12M 23/12; C12M 33/00
See application file for complete search history.

(56) References Cited

U.S. PATENT DOCUMENTS

2011/0042237 A1  2/2011  Fukuda et al.

FOREIGN PATENT DOCUMENTS

| JP | A 2005-27598 | 2/2005 |
| JP | A 2008-295382 | 12/2008 |
| WO | WO 2009/031375 A1 | 3/2009 |

OTHER PUBLICATIONS

Holmes, "Novel peptide-based biomaterial scaffolds for tissue engineering" (Jan. 2002) Trends in Biotechnology, vol. 20, No. 1:16-21.*
Kurihara & Nagamune, "Cell Adhesion Ability of Artificial Extracellular Matrix Proteins Containing a Long Repetitive Arg-Gly-Asp Sequence" (Mar. 2005) Journal of Bioscience and Bioengineering, vol. 100, No. 1: 82-87.*
Oct. 11, 2011 Search Report issued in International Patent Application No. PCT/JP2011/070533 (with translation).
Seto et al; "Engineering of capillary-like structures in tissue constructs by electrochemical detachment of cells;" Biomaterials 31; 2010; pp. 2209-2215.
Mochizuki et al; "Engineering of Thick Cell Sheets based on Electrochemical Desorption of Ogliopeptide on Porous Membrane Substrate;" The 42$^{nd}$ Abstracts of Autumn Meeting of the Society of Chemical Engineers; Japan; Sep. 6, 2010; p. 743, abstract only.
Mochizuki et al; "Takoshitsu Membrane o Mochiita Denki Kagakuteki Genri ni Motozuku Saibo Sheet Kaishu Gijutsu;" Regenerative Medicine; Feb. 1, 2011; vol. 10, extra special issue; p. 282, 2P-166, abstract only.
Mochizuki et al; "Engineering of Thick Cell Sheets based on Electrochemical Desorption of Ogliopeptide on Porous Membrane Substrate;" Dai 62 Kai Abstracts of the Annual Meeting of the Society for Biotechnology; Japan; Sep. 25, 2010; p. 174, 3P-2103, abstract only.
May 7, 2015 Search Report issued in European Application No. 11823655.3.
Termis—AP Sydney Conference, Sep. 1, 2010, http://www.termis.org/docs/termisAP2010_abstracts.pdf.
Kakegawa et al., "Cell-Adhesive and Cell-Repulsive Zwitterionic Oligopeptides for Micropatterning and Rapid Electrochemical Detachment of Cells", Tissue Engineering Part A, vol. 19, No. 1-2, Sep. 4, 2012, pp. 290-298.

* cited by examiner

Primary Examiner — Robert Yamasaki
Assistant Examiner — Teresa E Knight
(74) Attorney, Agent, or Firm — Oliff PLC

(57) ABSTRACT

There is provided a culture method and a culture device for efficiently producing cells and/or cell tissue suitable for medication applications. The culture method may include a first step of adhering the cells onto the electrode layer and culturing the cells thereon. The electrode layer may be coated with an oligopeptide including a terminal amino acid, a cell adhesive sequence, and an alternating sequence to be bound to the one end side of the cell-adhesive sequence. The alternating sequence may include a plurality of acidic amino acids and a plurality of basic amino acids that are alternately bound to each other one by one. The culture method may include a second step of applying, to the electrode layer having the cells adhered thereonto, an electrical potential inducing reductive desorption of the oligopeptide, to thereby detach the cells from the electrode layer.

12 Claims, 13 Drawing Sheets

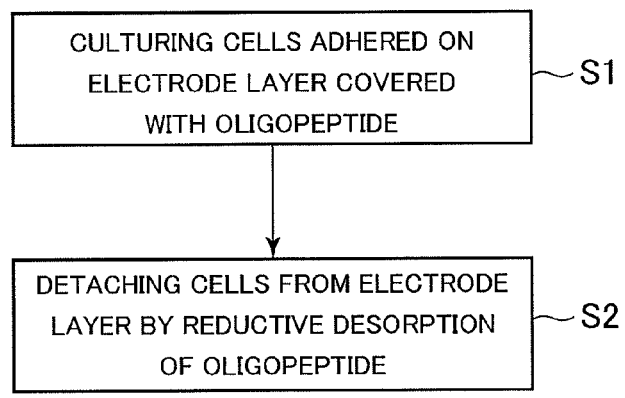
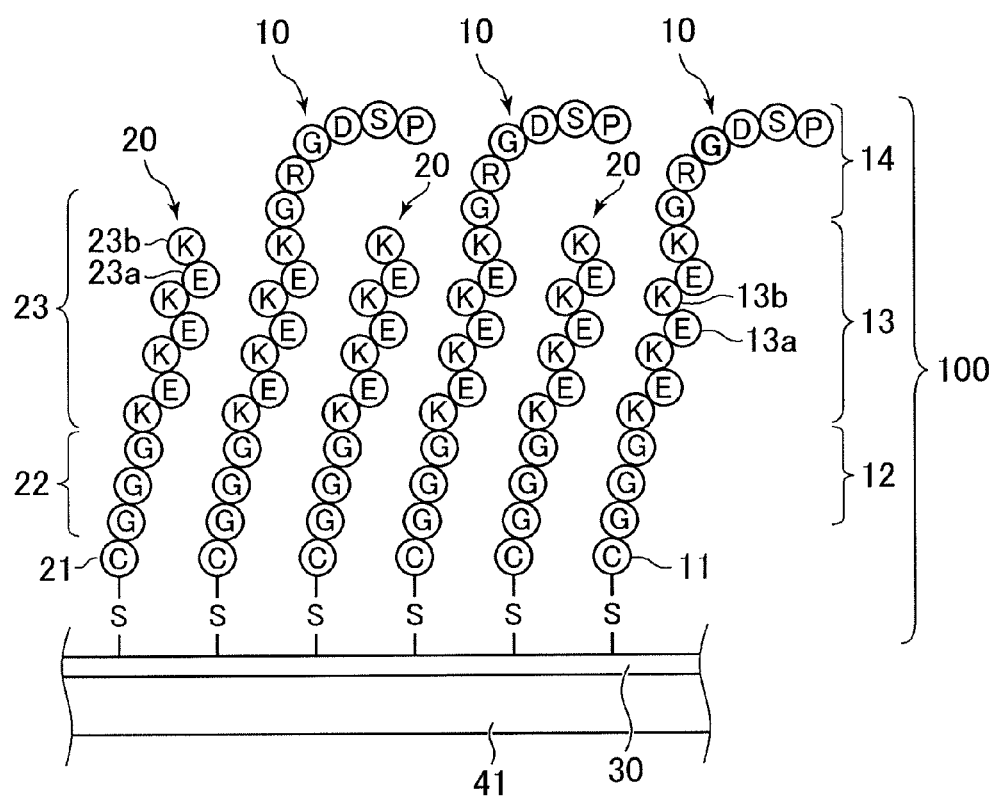

CULTURE METHOD AND CULTURE DEVICE FOR CULTURING CELLS ADHERED ONTO AN ELECTRODE LAYER

TECHNICAL FIELD

This invention relates to a culture method and culture device, and more particularly, to the production of cells and/or cell tissue suitable for medication applications.

BACKGROUND ART

A method using a proteolytic enzyme or a chelating agent, a method using magnetic force, a method using a thermoresponsive polymer, and a method using a photoresponsive polymer have been known in the prior art as methods for recovering cells that are adhered onto and cultured on the surface of a substrate.

However, the method using a proteolytic enzyme or a chelating agent damages cells. Further, in the method using magnetic force, cells need to be premagnetized. In the method using a thermoresponsive polymer or a photoresponsive polymer, temperature or light needs to be controlled throughout the culture period.

Patent Literature 1 thus proposes a method in which cells are adhered onto and cultured on the surface of an electrode on which a spacer material is bound via thiolate, and subsequently an electrical potential that induces reductive desorption of the spacer material is applied to the cell-adhering surface of the electrode to detach the cells from the surface of the electrode.

Further, Non Patent Literature 1 proposes a method in which cells are adhered onto the surface of gold via an oligopeptide containing a cell adhesion domain (RGD) in the center thereof and cysteine residues at both ends thereof and the cells are then detached from the surface of the gold by reductive desorption.

CITATION LIST

Patent Literature

[Patent Literature 1] JP 2008-295382 A

Non Patent Literature

[Non Patent Literature 1] Seto et al., Biomaterials, 2209-2215, 2010

SUMMARY OF INVENTION

Technical Problem

However, in the case of a spacer material (e.g., a cellular adhesive spacer material prepared by combining a cellular adhesion peptide to alkanethiol) which was used in Patent Literature 1, no evidence has been found to support the safety of cells or cell tissue bounded to such a spacer material in transplantation into a living body.

Further, the oligopeptide used in Non Patent Literature 1 was not self-organized on the surface of gold, and hence the oligopeptide did not form any dense layer on the surface of the gold. Accordingly, a substance such as a protein in a culture medium was non-specifically adsorbed to the surface of the gold. Thus in some cases, about 10% of cells adhered onto the surface of the gold remained without detachment even when an electrical potential was applied for 5 minutes.

This invention has been made in view of the above-mentioned problems, and one of the objects thereof is to provide a culture method and a culture device for efficiently producing cells and/or cell tissue suitable for medical applications.

Solution to Problem

A culture method according to an embodiment of this invention, in order to solve the above-mentioned problems, relates to a culture method of culturing cells adhered onto an electrode layer, the method including: a first step of adhering the cells onto the electrode layer and culturing the cells thereon, the electrode layer being coated with an oligopeptide including: a terminal amino acid forming one end thereof to be bound to the electrode layer via thiolate; a cell adhesive sequence forming another end thereof and having a cell-adhesive amino acid sequence; and an alternating sequence to be bound to the one end side of the cell-adhesive sequence, the alternating sequence including a plurality of acidic amino acids and a plurality of basic amino acids, being alternately bound to each other one by one; and a second step of applying, to the electrode layer having the cells adhered thereonto, an electrical potential inducing reductive desorption of the oligopeptide, to thereby detach the cells from the electrode layer. According to this invention, there is provided a culture method for efficiently producing cells and/or cell tissue suitable for medication applications.

Further, in the culture method, the electrode layer may be formed on a surface of a porous film held in a state of being suspended in a culture medium. Further, the configuration may be such that, in the first step, the cells are adhered onto the electrode and cultured thereon, to thereby form a cell tissue sheet adhered onto the electrode layer, and in the second step, an electrical potential inducing reductive desorption of the oligopeptide is applied to the electrode layer having the cell tissue sheet adhered thereonto, to thereby detach the cell tissue sheet from the electrode layer. In this case, the culture method may further include a third step of stacking a plurality of the cell tissue sheets each being caused to detach from the electrode layer to thereby form a laminate of the cell tissue sheets.

A culture device according to an embodiment of this invention in order to solve the above-mentioned problems relates to a culture device including an electrode layer for adhering cells thereonto and culturing the cells thereon, in which the electrode layer is coated with an oligopeptide including: a terminal amino acid forming one end thereof to be bound to the electrode layer via thiolate; a cell adhesive sequence forming another end thereof and having a cell-adhesive amino acid sequence; and an alternating sequence to be bound to the one end side of the cell-adhesive amino acid sequence, the alternating sequence including a plurality of acidic amino acids and a plurality of basic amino acids being alternately bound to each other one by one. According to this invention, there is provided a culture device for efficiently producing cells and/or a cell tissue suitable for medication applications.

Further, in the culture device, the electrode layer may be formed on a surface of a porous film held in a state of being suspended in a culture medium.

Advantageous Effects of Invention

According to this invention, there is provided a culture method and a culture device for efficiently producing cells and/or cell tissue suitable for medical applications.

BRIEF DESCRIPTION OF DRAWINGS

FIG. 1 is an explanatory diagram illustrating a principal step included in an example of a culture method according to an embodiment of this invention.

FIG. 2 is an explanatory diagram illustrating an example of an electrode layer coated with an oligopeptide, which is used in the embodiment of this invention.

DESCRIPTION OF EMBODIMENTS

Now, an embodiment of this invention will be described. Note that this invention is not limited to examples described in this embodiment.

Figure 3:
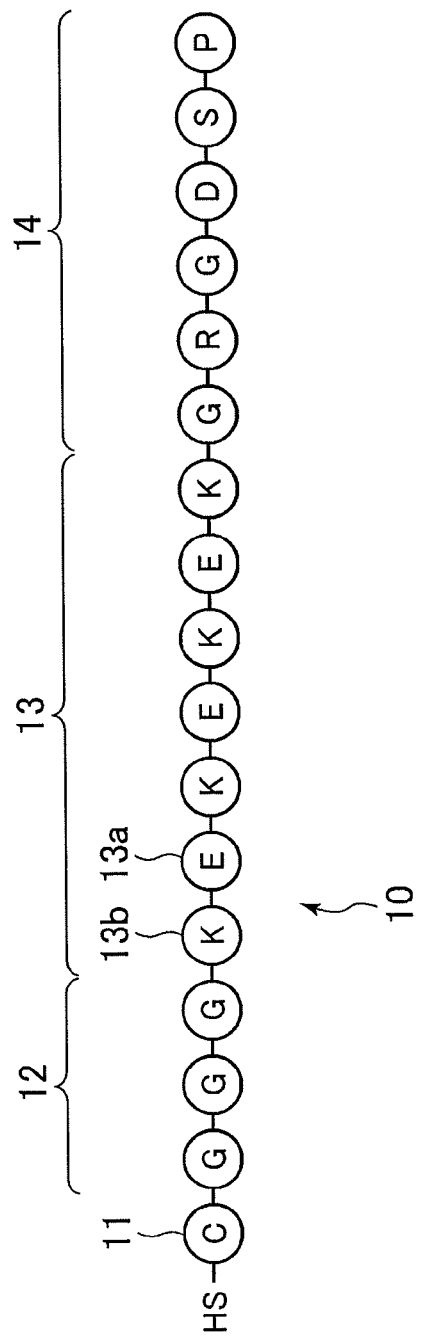
FIG. 3 is an explanatory diagram illustrating an example of an oligopeptide used in the embodiment of this invention.
Figure 4A:
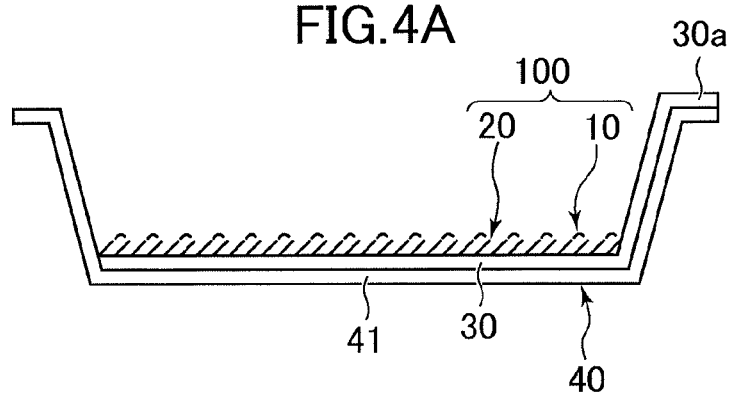
FIG. 4A is an explanatory diagram illustrating an example of an electrode layer used in the embodiment of this invention.
Figure 4B:
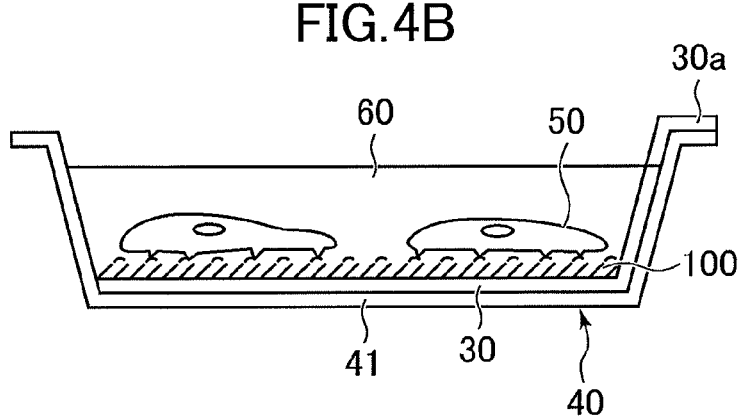
FIG. 4B is an explanatory diagram illustrating a state in which cells are adhered onto the electrode layer illustrated in FIG. 4A.
Figure 4C:
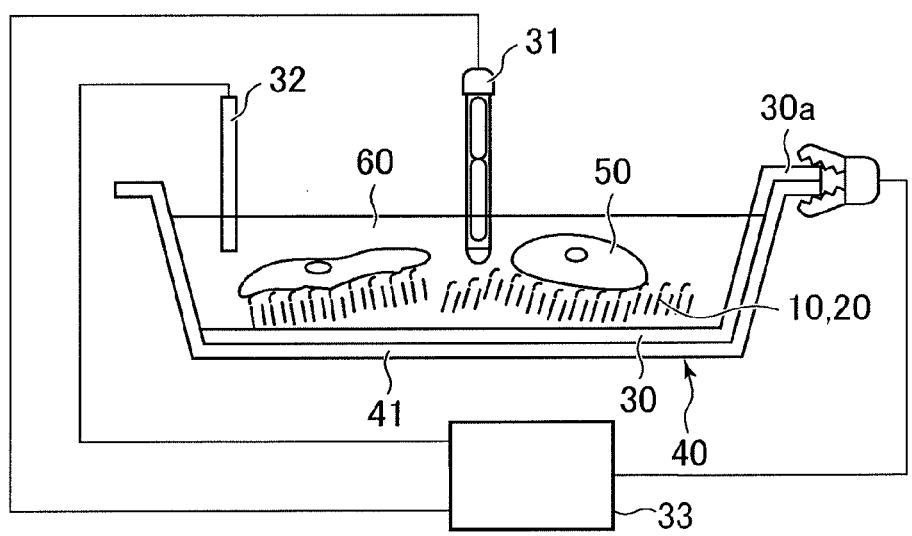
FIG. 4C is an explanatory diagram illustrating a state in which the cells are detached through application of an electrical potential onto the electrode layer illustrated in FIG. 4B.

FIG. 1 is an explanatory diagram illustrating a principal step included in an example of a culture method according to this embodiment (hereinafter referred to as "the method of this invention"). FIG. 2 is an explanatory diagram illustrating an example of an electrode layer coated with an oligopeptide, which is used in this embodiment. FIG. 3 is an explanatory diagram illustrating an example of an oligopeptide, which is used in this embodiment. FIGS. 4A to 4C are explanatory diagrams illustrating examples of a process for culturing and recovering cells in this embodiment.

The method of this invention is a method of culturing cells 50 adhered onto an electrode layer 30. The method includes: a first step (hereinafter referred to as "culture step S1) of adhering the cells 50 onto the electrode layer 30 and culturing the cells 50 thereon, the electrode layer 30 being coated with an oligopeptide (hereinafter referred to as "adhesive oligopeptide 10") including a terminal amino acid 11 forming one end thereof to be bound to the electrode layer 30 via thiolate, a cell adhesive sequence 14 forming another end thereof and having a cell-adhesive amino acid sequence, and an alternating sequence 13 to be bound to the one end side of the cell-adhesive sequence 14, the alternating sequence 13 including a plurality of acidic amino acids 13a and a plurality of basic amino acids 13b, being alternately bound to each other one by one; and a second step (hereinafter referred to as "detachment step S2" of applying, to the electrode layer 30 having the cells 50 adhered thereonto, an electrical potential inducing reductive desorption of the adhesive oligopeptide 10, to thereby detach the cells 50 from the electrode layer 30.

In the culture step S1, first, the electrode layer 30 coated with the adhesive oligopeptide 10 is prepared. The adhesive oligopeptide 10 is not particularly limited as long as the adhesive oligopeptide 10 has an amino acid sequence including the terminal amino acid 11, the alternating sequence 13, and the cell adhesive sequence 14 as described above.

The number of amino acids constituting the adhesive oligonucleotide 10 is not particularly limited. The adhesive oligopeptide 10 may be, for example, a peptide formed of 8 to 100 amino acids, preferably a peptide formed of 10 to 30 amino acids. In an example illustrated in FIG. 2 and FIG. 3, the adhesive oligopeptide 10 is a peptide formed of 17 amino acids.

It is preferred that the adhesive oligopeptide 10 be an oligopeptide that forms a self-assembled monolayer (SAM) on the electrode layer 30. In other words, it is preferred that the adhesive oligopeptide 10 has, for example, an alternating sequence 13 formed of 4 or more amino acids. In this case, an effective electrostatic interaction is generated between the molecules of the adhesive oligopeptides 10, and hence a self-assembled monolayer of the adhesive oligopeptide 10 is reliably formed on the electrode layer 30. In the example illustrated in FIG. 2 and FIGS. 4A to 4C, an oligopeptide layer 100 is formed on the electrode layer 30. The oligopeptide layer 100 is formed of a self-assembled monolayer composed of the adhesive oligopeptide 10 and coating the electrode layer 30.

The terminal amino acid 11 is not particularly limited as long as the terminal amino acid is an amino acid bound to the electrode layer 30 via thiolate. In other words, the terminal amino acid 11 is any amino acid having a functional group to form a binding to the electrode layer 30 via thiolate.

The functional group which forms thiolate may be one kind or more selected from the group consisting of, for example, a thiol group (—SH), a disulfide (—S—S—), and a sulfide (—S—). In the example illustrated in FIG. 2 and FIG. 3, the terminal amino acid 11 is cysteine (C), which forms the N terminal of the adhesive oligopeptide 10.

Because the adhesive oligopeptide 10 includes the terminal amino acid 11, coating of the electrode layer 30 with the adhesive oligopeptide 10 and reductive desorption of the adhesive oligopeptide 10, which will be described later, are efficiently carried out.

The cell adhesive sequence 14 is not particularly limited as long as the cell adhesive sequence 14 is a cell adhesive amino acid sequence. In other words, for example, the cell adhesive sequence 14 may include a specific amino acid sequence that is specifically bound to a molecule, such as a protein like integrin, or a sugar chain, found on the surface of the cells 50 used (hereinafter referred to as "specific amino sequence"). In the example illustrated in FIG. 2 and FIG. 3, the cell adhesive sequence 14 includes a so-called RGD sequence as a specific amino acid sequence, which forms the C terminal of the adhesive oligopeptide 10 and has its arginine (R), glycine (G), and aspartic acid (D) bound to each other.

The cell adhesive sequence 14 may be an amino acid sequence consisting of the specific amino sequence, or may be an amino acid sequence in which additional amino acid(s) is/are bound to the N terminal and/or the C terminal of the specific amino acid sequence.

As an amino acid other than the specific amino acids, which is included in the cell adhesive sequence 14, a neutral amino acid may be included. The neutral amino acid is one kind or more selected from the group consisting of alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), and valine (V).

In the example illustrated in FIG. 2 and FIG. 3, the cell adhesive sequence 14 includes the RGD sequence, glycine (G) bound to the N terminal of the RGD sequence, and serine (S) and proline (P) sequentially bound to the C terminal of the RGD sequence.

The number of amino acids constituting the cell adhesive sequence 14 is not particularly limited. The cell adhesive sequence 14 may be formed of, for example, 3 to 50 amino acids, preferably 5 to 25 amino acids. In the example illustrated in FIG. 2 and the FIG. 3, the cell adhesive sequence 14 is an amino acid sequence consisting of 6 amino acids.

Because the adhesive oligopeptide 10 includes the cell adhesive sequence 14, the cells 50 are reliably adhered onto the electrode layer 30 via the adhesive oligopeptide 10.

The alternating sequence 13 is not particularly limited as long as the alternating sequence 13 is an amino acid sequence including as a whole the plurality of acidic amino acids 13a and the plurality of basic amino acids 13b, being alternately bound to each other one by one.

For example, the acidic amino acid 13a may be one or two kinds selected from the group consisting of aspartic acid (D) and glutamic acid (E). The basic amino acid 13b may be, for example, one or more selected from the group consisting of lysine (K), arginine (R), and histidine (H). The alternating sequence 13 may include these acidic amino acids 13a and the base amino acids 13b in any combination.

In the example illustrated in FIG. 2 and FIG. 3, the alternating sequence 13 is an amino acid sequence bound to the N terminal of the cell adhesive sequence 14 and consisting of four lysines (K) and three glutamic acids (E) which are alternately bound one by one to each other.

In the alternating amino sequence 13, the number of the acidic amino acids 13a may be equal to or one more than the number of the basic amino acids 13b, and vice versa. Even if one of the number of the acidic amino acids 13a and the number of the basic amino acids 13b is one more than the other, for example, the alternating sequence 13 includes at least two of each of the acidic amino acids 13a and the basic amino acids 13b, and hence the tip portion (portion having four or more amino acids in total) of the alternating sequence 13 bound to the cell adhesive sequence 14 is electrically neutralized sufficiently.

The number of the amino acids constituting the alternating sequence 13 is not particularly limited. The alternating sequence 13 may be, for example, an amino acid sequence formed of 4 to 50 amino acids, preferably an amino acid sequence formed of 5 to 25 amino acids. In the example illustrated in FIG. 2 and FIG. 3, the alternating sequence 13 is an amino acid sequence formed of 7 amino acids, including three acidic amino acids 13a and four basic amino acids 13b.

Because the adhesive oligopeptide 10 includes the alternating sequence 13, for example, non-specific adsorption of any substance to promote cell adhesion, such as a protein, to the adhesive oligopeptide 10 or the electrode layer 30 is efficiently prevented or reduced.

The adhesive oligopeptide 10 may be a peptide consisting of an amino acid sequence where the above-mentioned terminal amino acid 11, alternating sequence 13, and cell adhesive sequence 14 are sequentially bound to each other to form the amino acid sequence.

The adhesive oligopeptide 10 may also include, for example, an intermediate sequence 12 interposed between the terminal amino acid 11 and the alternating sequence 13. The intermediate sequence 12 is not particularly limited as long as the intermediate sequence 12 is an amino acid sequence bound to the terminal amino acid 11 on one end thereof and bound to the alternating sequence 13 on another end.

It is preferred that the intermediate sequence 12 be composed of amino acids with relatively small molecular sizes. It is also preferred that the intermediate sequence 12 be composed of neutral amino acids as described above. In other words, the intermediate sequence 12 may be, for example, an amino acid sequence consisting of one or two kinds selected from the group consisting of alanine and glycine.

The number of amino acids constituting the intermediate sequence 12 is not particularly limited. The intermediate sequence 12 may be, for example, an amino acid sequence formed of 0 to 50 amino acids, and preferably an amino acid sequence formed of 2 to 10 amino acids. In the example illustrated in FIG. 2 and FIG. 3, the intermediate sequence 12 is an amino acid sequence where three glycines are bound together to form the amino acid sequence.

Because the adhesive oligopeptide 10 includes the intermediate sequence 12, an interaction between the cell adhesive sequence 14 and/or the alternating sequence 13 and the electrode layer 30 is efficiently prevented or reduced.

The electrode layer 30 is not particularly limited as long as the electrode layer 30 is a conductive layer, which allows the adhesive oligopeptide 10 to be bound to the surface thereof via thiolate while being able to be detached by reductive desorption, and functions as a working electrode in reductive desorption of the adhesive oligopeptide 10.

In other words, the electrode layer 30 may be, for example, a layer made of one or more kind of conductive materials selected from the group consisting of noble metals (e.g., gold, platinum, silver, and copper), semiconductors (e.g., silicon, zinc selenide, and silicon carbide), and metallic oxides (e.g., indium tin oxide, zinc oxide, and tin oxide). In the example illustrated in FIG. 2 and FIGS. 4A to 4C, the electrode layer 30 is a thin film made of a noble metal (e.g., gold).

As illustrated in FIG. 3, for example, coating of the electrode layer 30 with the adhesive oligopeptide 10 may be carried out using the free adhesive oligopeptide 10 having the terminal amino acid 11 containing a functional group that forms a binding to the electrode layer 30 via thiolate.

In other words, the free adhesive oligopeptide 10 and the electrode layer 30 are brought into contact with each other in a solution (e.g., the electrode layer 30 is soaked in a solution containing the free adhesive oligopeptide 10 and is maintained for a predetermined time). As illustrated in FIG. 2, the adhesive oligopeptide 10 is therefore allowed to spontaneously form thiolate between the adhesive oligopeptide 10 and the electrode layer 30, thereby being bound to the electrode layer 30.

The oligopeptide layer 100 formed on the electrode layer 30 may include, as illustrated in FIG. 2, in addition to the above-mentioned adhesive oligopeptide 10, another oligopeptide including the same amino acid sequence as that of the adhesive oligopeptide 10, except that the amino acid sequence does not include any cell adhesive amino acid sequence (hereinafter referred to as "non-adhesive oligopeptide 20").

The nonadhesive oligopeptide 20 is, as illustrated in FIG. 2, a peptide including a terminal amino acid 21 forming one end thereof to be bound to the electrode layer 30 via thiolate and an alternating sequence 23 forming another end, and including a plurality of acidic amino acids 23a and a plurality of basic amino acids 23b, being alternately bound to each other one by one.

It is preferred that the nonadhesive oligopeptide 20 has the alternating sequence 23 having the same amino acid sequence as that of the alternating sequence 13 of the adhesive oligopeptide 10. The nonadhesive oligopeptide 20 may also include the terminal amino acid 21 having the same amino acid sequence as that of the terminal amino acid 11 of the adhesive oligopeptide 10. In the example illustrated in FIG. 2, the amino acid sequences of the terminal amino acid 21 and the alternating sequence 23 of the nonadhesive oligopeptide 20 are the same as the amino acid sequences of the terminal amino acid 11 and the alternating sequence 13 of the adhesive oligopeptide 10, respectively.

Further, the alternating sequence 23 of the nonadhesive oligopeptide 20 forms the end portion of the nonadhesive oligopeptide 20. It is therefore preferred that, in the alternating sequence 23, one of the number of acetic amino acids 23a and the number of the basic amino acids 23b is one more than the other, so as to cancel out charge of amino acids constituting the free end of the alternating sequence 23 (i.e., the free end of the nonadhesive oligopeptide 20). In the example illustrated in FIG. 2, the alternating sequence 23 of the nonadhesive oligopeptide 20 consists of an amino acid sequence in which the number of lysine (K) is one more than the number of glutamic acid (E) so as to cancel out negative charge of lysine (K) constituting the free end (C terminal) of the alternating sequence 23. The alternating sequence 13 of the adhesive oligopeptide 10 has the same amino acid sequence as that of the alternating sequence 23 of the nonadhesive oligopeptide 20 designed as described above. As a result, the effective electrostatic interaction is generated between the molecule of the adhesive oligopeptide 10 and the molecule of the nonadhesive oligopeptide 20, which are adjacent to each other, or between the molecules of the adhesive oligopeptides 10 that are adjacent to each other, thereby forming an oligopeptide layer 100 formed of a self-assembled monolayer on the electrode layer 30.

The formation of the oligopeptide layer 100 including the nonadhesive oligopeptide 20 is carried out, for example, using the free nonadhesive oligopeptide, which has the terminal amino acid 21 containing a functional group being bound to the electrode layer 30 via thiolate, such as an oligopeptide consisting of an amino acid sequence which lacks the cell adhesive sequence 14 compared with the adhesive oligopeptide 10 as illustrated in FIG. 3.

In other words, for example, the oligopeptide peptide layer 100 is formed by soaking the electrode layer 30 in a solution containing the free adhesive oligopeptide 10 and the free nonadhesive oligopeptide 20 to bind the adhesive oligopeptide 10 and the nonadhesive oligopeptide 20 to the electrode layer 30 via thiolate, as illustrated in FIG. 2.

The electrode layer 30 coated with the adhesive oligopeptide 10 is also formed by using such a free nonadhesive oligopeptide 20. That is, for example, the electrode layer 30 is first coated with the nonadhesive oligopeptide 20 as described above. Subsequently, the nonadhesive oligopeptide 20 bound to the electrode layer 30 is chemically reacted with the free peptide containing the cell adhesive sequence 14 so as to bind the cell adhesive sequence 14 to the tip of the alternating sequence 23 of the nonadhesive oligopeptide 20. As a result, the electrode layer 30 coated with the adhesive oligopeptide 10 having the cell adhesive sequence 14 is obtained. In this way, the oligopeptide layer 100 containing the adhesive oligopeptide 10 is formed on the electrode layer 30.

In the example illustrated in FIG. 2, the oligopeptide layer 100 formed of the adhesive oligopeptide 10 and the nonadhesive oligopeptide 20 is formed. However, the oligopeptide layer 100 is not limited to this configuration. Alternatively, for example, the oligopeptide layer 100 formed of the adhesive oligopeptide 10 may be made.

In the case where the oligopeptide peptide layer 100 includes the nonadhesive oligopeptide 20 in addition to the adhesive oligopeptide 10, the adhesive properties of the cells 50 to the oligopeptide layer 100 is adjusted by changing a proportion of the adhesive oligopeptide 10 to the nonadhesive oligopeptide 20.

The proportion of the adhesive oligopeptide 10 to the non-adhesive oligopetide 20 (the content of the adhesive oligopeptide 10: the content of the nonadhesive oligopeptide 20) is appropriately determined depending on the degree of adhesiveness of the cells 50 to be achieved and the efficiency of detaching the cells 50. The proportion of the adhesive oligopeptide 10 to the nonadhesive oligopeptide 20 may be, for example, 0.1:100 to 100:0 in terms of mole ratio.

A culture device according to this embodiment (hereinafter referred to as the "device of this invention") includes the above-mentioned electrode layer 30 coated with the adhesive oligopeptide 10 as described above to adhere and culture the cells 50 thereon. The method of this invention is preferably employed using the device of this invention.

As illustrated in FIGS. 4A to 4C, the device of this invention includes the electrode layer 30 coated with the adhesive oligopeptide 10, and is also provided with a culture portion 40 that retains the cells 50 adhering onto the electrode layer 30 in a culture medium 60. The culture portion 40 is not particularly limited as long as the culture portion 40 is an instrument that contains a culture medium and the electrode layer 30 onto which the cells 50 are adhered. The culture portion 40 may be, for example, a culture vessel such as a culture dish. In an example illustrated in FIGS. 4A to 4C, the culture portion 40 is a culture dish.

In FIG. 2 and FIGS. 4A to 4C, the electrode layer 30 may be formed on the surface of a substrate 41. In other words, for example, the electrode layer 30 may be a conductive thin film formed on the surface of the substrate 41.

The substrate 41 is not particularly limited as long as the substrate 41 is made of a material capable of forming the electrode layer 30 on the surface thereof. In other words, for example, the substrate 41 may be an element made of a metal material, which is not necessarily one to be directly used as an electric material, and may be a nonmetal material, such as glass or a synthetic resin (e.g., polyethylene or polypropylene).

In order to observe the cells 50 on the electrode layer 30 with an optical microscope, the substrate 41 is preferably made of a transparent material. In the example illustrated in FIGS. 4A to 4C, the substrate 41 is the bottom of the culture dish molded with a transparent resin.

The shape of the substrate 41 is not particularly limited as long as the electrode layer 30 is formed on the surface thereof. In other words, the substrate 41 may be molded into the shape of, for example, a flat plate, a film, a mesh, or a bar. Further, the surface of the substrate 41 on which the electrode layer 30 is formed may be, for example, a flat surface, an irregular surface (e.g., a porous material surface), or a curved surface. In the example illustrated in FIGS. 4A to 4C, the substrate 41 is a flat-plate shaped structural component, and the electrode layer 30 is formed on the flat surface thereof.

As illustrated in FIGS. 4A to 4C, the culture portion 40 may have an electrical contact portion 30a that is electrically connected to the electrode layer 30 so as to apply an electrical potential to the electrode layer 30. The arrangement of the electrical contact portion 30a is not particularly limited as long as the electrical contact portion 30a is electrically connected to the electrode layer 30 so as to apply an electrical potential to the electrode layer 30. In other words, the electrical contact portion 30a is formed on, for example, part of the culture portion 40, which is not soaked in the culture medium 60 so as to be electrically connected to the electrode layer 30 soaked in the culture medium 60.

In the example illustrated in FIGS. 4A to 4C, the electrical contact portion 30a is formed in such a manner that the electrical contact portion 30a extends from the electrode 30, which is formed on the bottom surface of the culture dish of the culture portion 40 and soaked in the culture medium 60, to the side wall of the culture dish, which is not soaked in the culture medium 60.

The material of the electrical contact portion 30a is not particularly limited as long as the material is a conductive material. The material may be, for example, the same material as that of the above-mentioned electrode layer 30. In the example illustrated in FIGS. 4A to 4C, the electrical contact portion 30a is a thin film made of the same noble metal (e.g., gold) as that of the electrode layer 30.

The culture step S1 of the method of this invention preferably uses the above-mentioned device of this invention to adhere the cells 50 to the electrode layer 30 covered with the adhesive oligopeptide 10 and culture the cells 50 thereon.

The cells 50 are not particularly limited as long as the cells 50 are cells capable of being adhered onto the electrode layer 30 via the adhesive oligopeptide 10. In other words, the useable cells may be cells of a human being or an animal other than a human being (e.g., monkey, pig, canine, rat, or mouse), which are derived from any organ or tissue (e.g., liver, heart, pancreas, kidneys, brain, nerve, skin, or blood).

Specifically, for example, usable cells may be primary culture cells harvested from an organ or tissue by an enzyme treatment or from the blood by separation, or an established cell line established therefrom. Alternatively, the usable cells include not only differentiated cells but also undifferentiated cells such as embryonic stem cells or pluripotent stem cells. These cells may be further subjected to artificial handling such as genetic manipulation before being used. The useable cells may be, for example, induced pluripotent stem (iPS) cells or may be those differentiated from the iPS cells.

In the case of recovering and using the cells 50 cultured by the method of this invention and the device of this invention and/or cell tissues formed from the cells 50 in medical field technology (e.g., regenerative medicine or artificial organ), cells of a human being or a mammal other than a human being are preferably used, and human-derived cells are more preferably used.

The cells 50 may be adhesive cells that require scaffold for survival and growth or nonadhesive cells that do not require scaffold for survival and growth. The adhesive cells are preferably used. In the culture step S1, as described later, in the case of culturing a cell tissue in which the cells 50 are two- or three-dimensionally accumulated, cells capable of being bound to each other to form an assembly of the cells 50 are preferably used. As the cells 50, one kind of cell may be used alone. Alternatively, a cell group in which two or more kinds of cells are mixed in any numerical proportion may be used.

The culture of the cells 50 on the electrode layer 30 may be performed by adhering the cells 50 to the electrode layer 30 in the culture medium 60 and keeping the cells 50 at a predetermined temperature (e.g., 37° C.) for a predetermined time period (e.g., several hours to several weeks or several months). Specifically, for example, the culture portion 40 having the electrode layer 30 as illustrated in FIG. 4A is first prepared. The culture medium 60 with dispersed cells 50 is then poured into the culture portion 40, and left stationary for several hours at 37° C. As a result, as illustrated in 4B, the cells 50 are adhered onto the electrode layer 30 via the oligopeptide layer 100 in the culture medium 60.

The culture medium 60 is not particularly limited as long as the culture medium 60 is an aqueous solution containing required salts, nutrient components, and the like at suitable concentrations to maintain the survival state, functions, and the like of the cells 50. Specifically, for example, the culture medium 60 may be a culture medium in which antibiotics and the like are added to a basic medium such as a Dulbecco's modified eagle's medium (DMEM) or may be an aqueous solution of phosphate buffered saline (PBS) or the like.

The cells 50 adhered onto the electric layer 30 typically change their shapes from a sphere shape to a comparatively flat shape with culture time. During the culture period, the cells 50 consume nutrients and oxygen in the culture medium 60 and perform their metabolic activities such as protein secretion. If the cells 50 have growth abilities, the cells 50 may grow two- or three-dimensionally along the electrode layer 30 in an overlapping manner.

In the subsequent detachment step S2, an electrical potential causing reductive desorption of the adhesive oligopeptide 10 is applied to the electrode layer 30 onto which the cells 50 are adhered, and the cells 50 are detached from the electrode layer 30. In other words, an electrical potential is applied to the electrode layer 30 onto which the cells 50 are adhered via the adhesive oligopeptide 10 to cause reductive desorption of the adhesive oligopeptide 10.

The electrical potential to be applied to the electrode layer 30 is not particularly limited as long as the electrical potential falls within a range that does not exert any adverse effect on the cells 50 while reductive desorption of the adhesive oligopeptide 10 occurs. For example, the electrical potential may be a peak electrical potential for reductive desorption of the adhesive oligopeptide 10 or an electrical potential more negative than the peak electrical potential for reductive desorption.

The peak electrical potential for reductive desorption may be determined as a value peculiar to the adhesive oligopeptide 10 to be used. In other words, for example, when the electrical potential is applied to the electrode layer 30, onto which the adhesive oligopeptide 10 is bound, while being gradually changed from the predetermined upper limit electrical potential to the predetermined lower limit electrical potential, an electrical potential at which a reduction current passes through the electrode layer 30 is determined as a peak electrical potential for reductive desorption of the adhesive oligopeptide 10.

Specifically, for example, an electrical potential is applied to the electrode layer 30 by sweeping using a cyclic voltammetry (CV) at a predetermined sweep rate (a rate of electrical potential change) from a predetermined initial electrical potential to a predetermined reverse electrical potential and then an electrical potential is applied again at the predetermined sweep rate in reverse, namely from the reverse electrical potential to the initial electrical potential. During this one cycle, the current passing through the electrode layer 30 is measured. Subsequently, in a cyclic voltammogram representing the relationship between the applied electrical potential and the detected current value, which is obtained as a result of the measurement, an applied electrical potential at which a negative current peak indicating a reduction current is generated is determined as a peak electrical potential for reductive desorption.

The electrical potential to be applied to the electrode layer 30 may be within a range of electrical potential window. In other words, a usable electrical potential is more negative than a peak electrical potential for reductive desorption of the adhesive oligopeptide 10 and within a range of electrical potential window. Note that, even in the case of falling out of the range of electrical potential window, any electrical potential may be used for reductive desorption as long as the electrical potential is within a range not affecting the cells 50.

The peak electrical potential for reductive desorption varies depending on the kind of the adhesive oligopeptide 10 to be used. As a an applied electrical potential in the detachment step S2, for example, one in a range of from −0.1 V to −2.0 V (vs Ag/AgCl) may be used, and preferably one in a range of from −0.5 V to −1.5 V (vs Ag/AgCl) may be used. In the case of applying an electrical potential more negative than the peak electrical potential for reductive desorption to the electrode surface, for example, it is preferred that an electrical potential to be used is 0.05 V to 0.5 V more negative than the peak electrical potential of the reductive desorption.

Further, in the case of using the above-mentioned nonadhesive oligopeptide 20 in addition to the adhesive oligopeptide 10, an electrical potential that allows both the adhesive oligopeptide 10 and the nonadhesive oligopeptide 20 to be reduced and desorbed is applied to the electrode layer 30. In other words, for example, it is possible to use an electrical potential of the peak electrical potential for reductive desorption of the adhesive oligopeptide 10 and the peak electrical potential for reductive desorption of the nonadhesive oligopeptide 20.

Further, in the case where the amino acid sequence of the adhesive oligopeptide 10 and the amino acid sequence of the nonadhesive oligopeptide 20 are identical or similar to each other, for example, in the case where the amino acid sequence of the nonadhesive oligopeptide 20 is identical to that of the adhesive oligopeptide 10 except that the former does not include the cell adhesive sequence 14, there is no significant difference between the peak electrical potential for reductive desorption of the adhesive oligopeptide 10 and the peak electrical potential for reductive desorption for the nonadhesive oligopeptide 20 (i.e., a shift in the peak electrical potential for reductive desorption caused by a difference of the presence or absence of the cell adhesive sequence 14 is small). Thus, a suitable electrical potential is easily determined.

Therefore, in the case of using a combination of two kinds of oligopeptides, the adhesive oligopeptide 10 and the nonadhesive oligopeptide 20, as described above, a usable applied electrical potential may be, for example, one in a range of from −0.1 V to −2.0 V (vs Ag/AgCl), preferably one in a range of from −0.5 V to −1.5 V (vs Ag/AgCl). In the case of applying an electrical potential more negative than the peak electrical potential for reductive desorption to the electrode surface, for example, it is preferred that an electrical potential to be used be preferably 0.05 V to 0.5 V more negative than the peak electrical potential of the reductive desorption.

Application of an electrical potential to the electrode layer 30 for reductive desorption of the adhesive oligopeptide 10 may be performed by, for example, scanning application in a manner similar to the above-mentioned case where the peak electrical potential for reductive desorption is determined. Here, in the scanning application, the electrical potential is changed at a predetermined sweep rate in a predetermined electrical potential range including a peak electrical potential for reductive desorption.

Alternatively, the application of an electrical potential to the electrode layer 30 may be performed by, for example, a continuous application in which a constant electrical potential more negative than the peak electrical potential for reductive desorption or the peak electrical potential for the reduction electrical potential is continuously applied. In other words, the electrical potential to be applied is fixed to be constant and the constant electrical potential to be applied is then maintained for a predetermined time period.

Particularly, in this case, it is preferred that the constant electrical potential more negative than the peak electrical potential for reductive desorption be continuously applied throughout the predetermined time period. In this way, the peak electrical potential for the reductive desorption or the electrical potential more negative than the peak electrical potential for reductive desorption may be reliably applied to the entire electrode layer 30.

In the case of performing application of such an electrical potential using the device of this invention, the device of this invention may have, in addition to the culture portion 40, an electrode system including the electrode layer 30 as the working electrode. Specifically, in the example illustrated in FIG. 4C, the device of this invention has a three-electrode system including the electrode layer 30 as the working electrode, a reference electrode 31, and a counter electrode 32.

The reference electrode 31 is not particularly limited as long as the reference electrode 31 serves as a reference electrode. The reference electrode 31 may be, for example, a silver/silver chloride electrode (Ag/AgCl). The counter electrode 32 is not particularly limited as long as the counter electrode 32 serves as a counter electrode. The counter electrode 32 may be, for example, a platinum electrode. Note that the device of this invention may have a two-electrode system including the electrode layer 30 as a working layer and either the reference electrode 31 or the counter electrode 32.

As illustrated in FIG. 4C, the device of this invention may further include an electrical potential-applying portion 33 that applies an electrical potential for reductive desorption of the adhesive oligopeptide 10 to the electrode layer 30. As the electrical potential-applying portion 33, a cyclic voltammetry unit may be used, for example.

In this case, in the detachment step S2, the electrical potential-applying portion 33 is first electrically connected to the electrode layer 30 soaked in the culture medium 60 and having the cells 50 adhered thereonto. In the example illustrated in FIG. 4C, the electrical contact portion 30a, which is electrically connected to the electrode layer 30 and extends out of the culture medium 60, is electrically connected to the electrical potential-applying portion 33.

Further, in the example illustrated in FIG. 4C, both the reference electrode 31 and the counter electrode 32, which are electrically connected to the electrical potential-applying portion 33, are soaked into the culture medium 60. In the case of using the two-electrode system, only one of the reference electrode 31 and the counter electrode 32 (e.g., only the reference electrode 31) may be soaked into the culture medium 60.

Subsequently, the electrical potential-applying portion 33 is allowed to apply an electrical potential to the electrode layer 30. For instance, the electrical potential-applying portion 33 may apply a sweeping electrical potential to the electrode layer 30 while changing the electrical potential in a predetermined electrical potential range including the peak electrical potential for reductive desorption at a predetermined sweep rate. Alternatively, for example, the electrical potential-applying portion 33 may continuously apply the peak electrical potential for reductive desorption or any constant electrical potential more negative than the peak electrical potential for reductive desorption to the electrode layer 30.

In the detachment step S2, the electrical potential application as described above desorbs the adhesive oligopeptide 10 from the electrode layer 30 and therefore detaches the cells 50 adhered onto the electrode layer 30 via the adhesive oligopeptide 10.

Specifically, as illustrated in FIG. 4B, in the case where the cells 50 are adhered onto the electrode layer 30 while the cells 50 are in a dispersed state in which they do not bind to one another, the reductive desorption of the adhesive oligopeptide 10 leads to detachment of the cells 50 in the dispersed state from the electrode layer 30 as illustrated in FIG. 4C. In this case, therefore, the individual cells 50, which are in the dispersed state and are suspended in the culture medium 60, are recovered.

In the case of performing a scanning electrical potential application, the cells 50 are efficiently detached from the electrode layer 30 by repeatedly carrying out a sweeping cycle of an initial electrical potential and a reverse electrical potential. In addition, in the case of continuous electrical potential application, the cells 50 are detached from the electrode layer 30 more efficiently compared to the scanning electrical potential application. In particular, continuous application of a constant electrical potential more negative than the peak electrical potential for reductive desorption efficiently and reliably detaches the cells 50 from the electrode layer 30. Further, the electrical potential may be applied at a high frequency in the form of a square wave or the like.

Figure 5A:
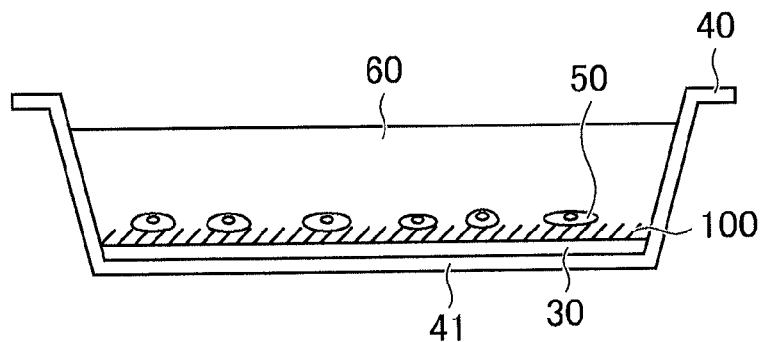
FIG. 5A is an explanatory diagram illustrating a state in which the cells are cultured on the electrode layer for forming a cell tissue sheet in the embodiment of this invention.
Figure 5B:
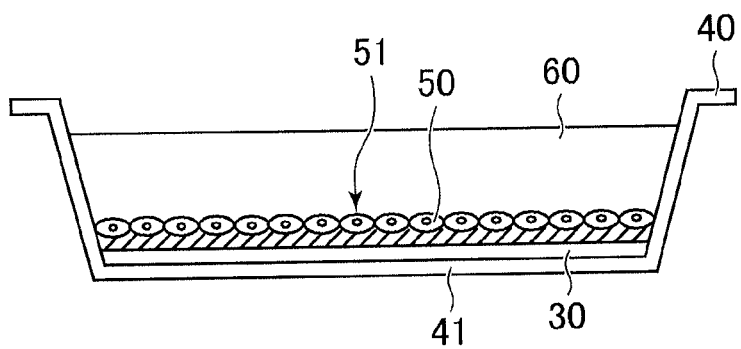
FIG. 5B is an explanatory diagram illustrating a state in which the cell tissue sheet is formed by culturing the cells illustrated in FIG. 5A.
Figure 5C:
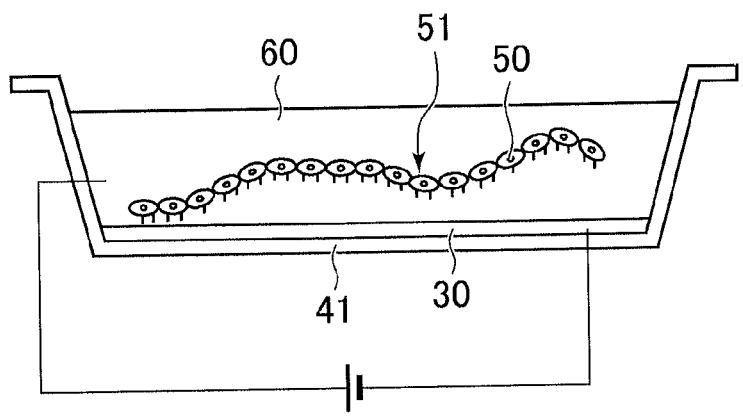
FIG. 5C is an explanatory diagram illustrating a state in which the cell tissue sheet is detached through application of an electrical potential onto the electrode layer illustrated in FIG. 5B.

In the method of this invention, further, cell tissue may be produced such that the cells 50 bind to one another and gather in a two- or three-dimensional manner. FIGS. 5A to 5C are explanatory diagrams illustrating an example of a process for culturing and recovering cell tissues in this embodiment. In an example illustrated in FIGS. 5A to 5C, a sheet-shaped cell tissue (hereinafter referred to as a "cell tissue sheet 51") is produced.

Specifically, in the culturing step S1, the cells 50 are adhered onto the electrode layer 30 coated with the adhesive oligopeptide 10 (see FIG. 2) and then cultured (FIG. 5A) to form a cell tissue sheet 51 adhered onto the electrode layer 30 (FIG. 5B). Next, in the detachment step S2, the cell tissue sheet 51 is detached from the electrode layer 30 through application of an electrical potential for reductive desorption of the adhesive oligopeptide 10 to the electrode layer 30 the cell tissue sheet 51 is adhered to (FIG. 5C).

Particularly, in the culturing step S1, first, individual cells 50 dispersed in the culture medium 60 are adhered onto the electrode layer 30 via the oligopeptide layer 100 and then cultured as illustrated in FIG. 5A. The cells 50 grow with culture time, spreading along the electrode layer 30. As a result, as illustrated in FIG. 5B, the grown cells 50 bind to one another and form the cell tissue sheet 51 bound to the electrode layer 30 via the oligopeptide layer 100. Further, in the case of using the cells 50 which do not grow, for example, the cell tissue body 51 of the cells bound to one another are formed by inoculating the cells 50 at a relatively high density on the electrode layer 30 and then culturing the cells 50.

In the detachment step S2, as illustrated in FIG. 5C, an electrical potential, which allows the adhesive oligopeptide 10 and the nonadhesive oligopeptide 20 forming the oligopeptide layer 100 to be reduced and desorbed, is applied to the electrode layer 30 to detach the cell tissue sheet 51 from the electrode 30 in addition to desorption of the adhesive oligopeptide 10 and the nonadhesive oligopeptide 20.

Here, in the case that the cell tissue sheet 51, which is constructed of a plurality of cells 50 which are two- or three-dimensionally bound to one another, is adhered onto the electrode layer 30, many cells 50 in the cell tissue sheet 51 are adhered onto the electrode layer 30. To efficiently detach the cell tissue sheet 51 from the electrode layer 30, most of the many adhered cells 50 need to be simultaneously detached.

In this regard, for example, the method of this invention allows the cell tissue sheet 51 to be efficiently detached from the electrode layer 30 by continuously applying a constant electrical potential, which is more negative than the peak electrical potential for reductive desorption of the adhesive oligopeptide 10, to the electrode layer 30. The detached cell tissue sheet 51 is suspended in the culture medium 60, and hence it is easily recovered.

The cell tissue manufactured by the method of this invention is not limited to the above-mentioned cell tissue sheet 51 as long as it is an aggregate of a plurality of cells 50. In other words, for example, a dome-shaped or spherical tissue (so-called spheroid), which is formed such that the cells 50 are aggregated while three-dimensionally grown on the electrode layer 30, may be cultured and recovered in a manner similar to the case of the above-mentioned cell tissue sheet 51.

Here, for example, in the case of covering the electrode layer 30 with oligopetides lacking in self-organizing ability, proteins in the culture medium 60 and proteins secreted from the cells 50 are adsorbed on the electrode layer 30 through gaps among the oligopeptides. As a result the cells 50 are strongly adhered onto the electrode layer 30 via the proteins. In this case, even if an electrical potential for reductive desorption of oligopeptide is applied to the electrode layer 30, it is difficult to efficiently detach the cells 50 from the electrode layer 30 in a short time.

On the other hand, in the electrode layer 30 covered with the above-mentioned adhesive oligopeptide 10, a self-assembled monolayer (e.g., oligopeptide layer 100 illustrated in FIG. 2) containing the adhesive oligopeptide 10 is formed due to the presence of the alternating sequence 13 in the adhesive oligopeptide 10. Consequently, nonspecific adsorption of protein to the adhesive oligopeptide 10 and the electrode layer 30, as well as nonspecific adsorption of the cells 50 to the electrode layer 30, are efficiently avoided or reduced.

The cells 50 adhered onto the electrode layer 30 via the adhesive oligopeptide 10 are therefore efficiently desorbed in a short time through application of an electrical potential for reductive desorption of the adhesive oligopeptide 10 to the electrode layer 30.

Further, the adhesive oligopeptide 10 desorbed from the electrode layer 30 binds to the cells 50 and the cell tissue cultured and recovered by the method of this invention and the device of this invention, via the cell adhesive sequence 14. For example, therefore, a problem may arise in safety of transplantation of the cells 50 and/or the cell tissue bound with the adhesive oligopeptide 10 into the living body (of a human or an animal other than a human). Such a problem in safety also occurs, for example, in transplantation of cells and cell tissues bound with alkanethiol and other polymer materials.

In this regard, the adhesive oligopeptide 10 has higher biocompatibility than any molecule not present in the living body, such as alkanethiol. In other words, substances generated by decomposition of the adhesive oligopeptide 10 are only amino acids. The cells 50 and the cell tissue produced by the method of this invention and the device of this invention are therefore suitable for medical applications because of their high biocompatibility, such as high safety in transplantation into the living body.

Further, the cells 50 and the cell tissue are noninvasively recovered without using any proteolytic enzyme and chelating agent. The recovered cells 50 and the recovered cell tissue are therefore prevented from having their metabolic activities and desired functions impaired, and keep their desired characteristics suitable for transplantation into the living body and other applications.

According to the method of this invention and the device of this invention, therefore, the cells 50 and the cell tissue suitable for medical applications such as regenerative therapies and artificial organs are efficiently produced. Note that the cells 50 and the cell tissue produced by the method of this invention and the device of this invention are supplied for not only medical applications but for any other applications. Specifically, for example, the cells 50 and the cell tissue are also used as various research tools for drug metabolism models in alternatives to animal testing and the like.

As illustrated in FIG. 6 and FIGS. 7A to 7C, the electrode layer 30 may be formed on the surface of a porous film 70 held in a state of being suspended in the culture medium 60. Specifically, in the example illustrated in FIG. 6, the porous film 70 is a film having a porous structure in which a large number of pores 73 are formed so that the pores communicate from one surface of the film (hereinafter referred to as "upper surface 71") to the other surface thereof (hereinafter, also referred to as an "under surface 72"). In the electrode layer 30 formed on the upper surface 71 of the porous film 70, openings are formed corresponding to the pores 73 of the porous film 70.

Figure 6:
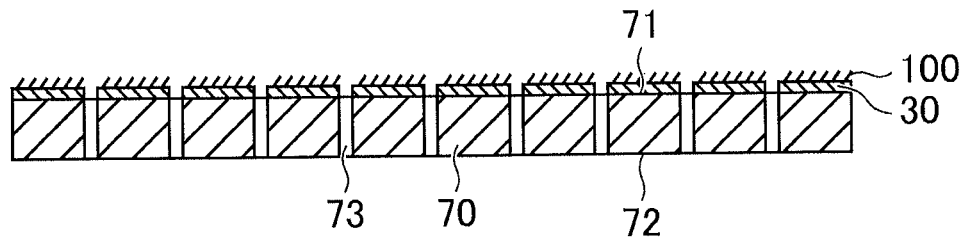
FIG. 6 is an explanatory diagram illustrating an example of an electrode layer formed on a porous film used in the embodiment of this invention.

The porous film 70 is not particularly limited as long as the porous film 70 allows the electrode layer 30 to be formed on the upper surface 71 thereof. In other words, for example, as illustrated in FIG. 6, the porous film 70 having a flat upper surface 71 with pores 73 formed and penetrated from the upper surface 71 to the under surface 72 may be preferably used.

The material of the porous film 70 is not particularly limited as long as it is suitable for culture of the cells 50. Examples of the materials include a resin, such as polyethylene terephthalate (PET) and polyurethane, and metal thin films. The size of the pores 73 formed in the porous film 70 is not particularly limited as long as the size of the pores 73 is within a range that prevents the cells 50 from passing through the pores 73. The pores 73 may have a diameter of 0.1 to 3 μm, for example. The aperture of the porous film 70 is not particularly limited, and it may be, for example, 1 to 25%.

Figure 7A:
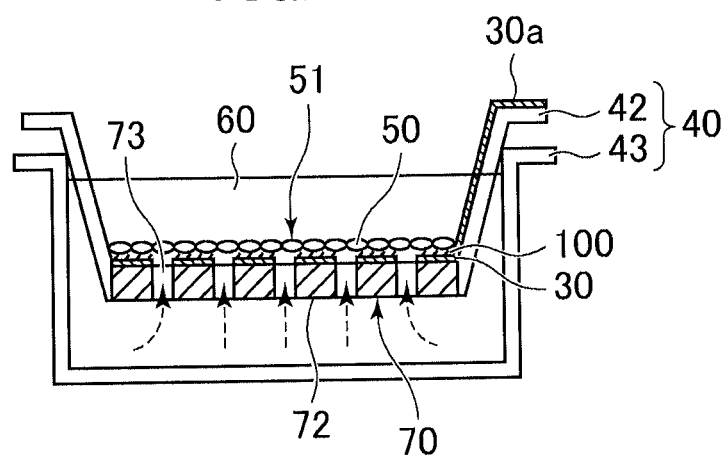
FIG. 7A is an explanatory diagram illustrating a state of culturing the cell tissue sheet that is adhered onto the electrode layer formed on the porous film in the embodiment of this invention.
Figure 7B:
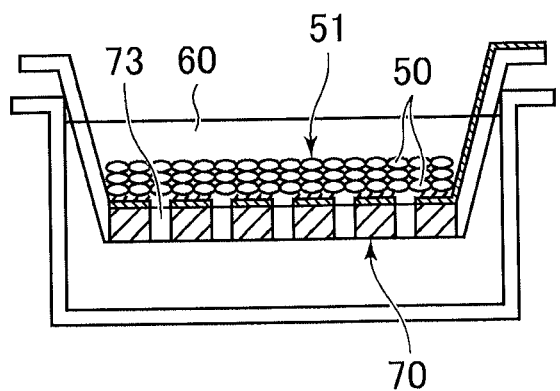
FIG. 7B is an explanatory diagram illustrating a state in which a thicker cell tissue sheet is formed by culturing the cell tissue sheet illustrated in FIG. 7A.
Figure 7C:
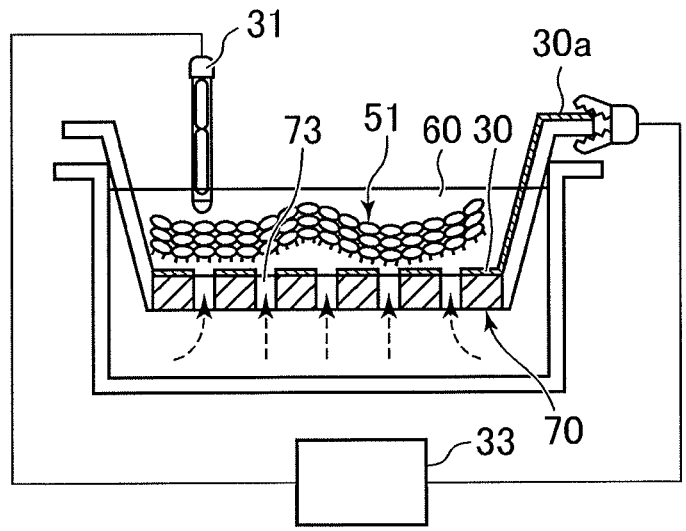
FIG. 7C is an explanatory diagram illustrating a state in which the cell tissue sheet is detached through application of an electrical potential onto the electrode layer on the porous film illustrated in FIG. 7B.

The porous film 70 is kept in a state of being suspended in the culture medium 60 as illustrated in FIG. 7A to FIG. 7C. In other words, the porous film 70 is brought into contact with the culture medium 60 not only at its upper surface 71 (on the electrode layer 30 side) but also at its opposite under surface 72.

In particular, in the example illustrated in FIGS. 7A to 7C, the culture portion 40 of this device includes a first culture vessel 42 having as a bottom portion the porous film 70 provided with the electrode layer 30, and a second culture vessel 43 supporting the first culture vessel 42 so that the porous film 70 is kept in a state of being suspended in the culture medium 60. As a result, the culture medium 60 is also supplied from the under surface 72 into the pores 73 of the porous film 70.

In the culture step S1 of the method of this invention, first, as illustrated in FIG. 7A, the cell tissue sheet 51 adhered onto the electrode layer 30 is formed by adhering the cells 50 to the electrode layer 30 of the porous film 70 kept in a state of being suspended in the culture medium 60, and culturing the cells 50.

Here, the cell tissue sheet 51 is one prepared by a dense aggregation of a large number of cells 50. Therefore, for example, if nutrients and oxygen are supplied from only one surface (surface opposite to the electrode layer 30) of the cell tissue sheet 51, cells inside the cell tissue sheet 51 may necrotize as the thickness of the cell tissue sheet 51 increases, as illustrated in FIG. 5A to 5C. In this case, therefore, there is a limit to increasing of the thickness of the cell tissue sheet 51. In other words, the cell tissue sheet 51 having a certain thickness or more is not formed.

In this regard, in the example illustrated in FIGS. 7A to 7C, the electrode layer 30 is formed on the porous film 70 kept in a state of being suspended in the culture medium 60. As illustrated by a broken arrow line in FIG. 7A, therefore nutrients and oxygen in the culture medium 60 are efficiently supplied also from the under surface 72 of the porous film 70 through a large number of pores 73 to the cell tissue sheet 51 adhered onto the electrode layer 30. As a result, as illustrated in FIG. 7B, the cells 50 forming the cell tissue sheet 51 are three-dimensionally grown to form the cell tissue sheet 51 having a larger thickness (i.e., having more layers of the cells 50) compared with the case illustrated in FIGS. 5A to 5C.

In the subsequent detachment step S2, as illustrated in FIG. 7C, the cell tissue sheet 51 is detached from the electrode layer 30 through application of an electrical potential for reductive desorption of the adhesive oligopeptide 10 to the electrode layer 30 which the cell tissue sheet 51 is adhered to.

Specifically, in the example illustrated in FIG. 7C, an electrical potential is applied to the electrode layer 30 by electrically connecting the electrode layer 30 to the electrical potential-applying portion 33 and soaking the reference electrode 31 electrically connected to the electrical potential-applying portion 33 into the culture medium 60. In the example illustrated in FIG. 7C, further, the first culture vessel 42 has the electrical contact portion 30a outside the culture medium 60 in a manner similar to the example illustrated in FIGS. 4A to 4C. When applying an electrical potential to the electrode layer 30, therefore, the electrical contact portion 30a and the electrical potential-applying portion 33 are electrically connected to each other.

Here, for reductive desorption of the adhesive oligopeptide 10, it is preferred that an electrical resistance of the cell tissue sheet 51 present between the electrode layer 30 bound to the adhesive oligopeptide 10 and the reference electrode 31 (and the counter electrode 32) be as small as possible.

However, in the case illustrated in FIGS. 5A to 5C, for example, the cell tissue sheet 51 causes a large electrical resistance. An appropriate electrical potential is therefore applied to only a part of the electrode layer 30 adhered onto the perimeter of the cell tissue sheet 51. As a result, the adhesive oligopeptide 10 is desorbed only from such a part of the electrode layer 30. Thus, the cell tissue sheet 51 may be gradually detached from the perimeter thereof.

In contrast, in the case that the electrode layer 30 is formed on the porous film 70 kept in a state of being suspended in the culture medium 60 as illustrated in FIG. 7A to FIG. 7C, the electrical resistance of the cell tissue sheet 51 is efficiently reduced in comparison with the case illustrated in FIG. 5A to FIG. 5C. As indicated by a broken-line arrow in FIG. 7C, therefore, an appropriate electrical potential is applied to the entire electrode layer 30 where the cell tissue sheet 51 is adhered thereto via a large number of pores 73 from the under surface 72 of the porous film 70. The adhesive oligopeptide 10 is thus desorbed throughout the electrode layer 30. Compared with the case illustrated in FIGS. 5A to 5C, therefore, the detachment of the cell tissue sheet 51 is more efficiently achieved in a short time.

Accordingly, the use of the porous film 70 as a substrate forming the electrode layer 30 detaches the thick cell tissue sheet 51, which has been difficult to detach in the prior art, in a shorter time than the conventionally.

When the cell tissue sheet 51 is recovered, the cell tissue sheet 51 adhered onto the upper surface 71 of the porous film 70 is efficiently recovered by flushing the culture medium 60 from the under surface 72 to the upper surface 71 of the porous film 70 via the pores 73 thereof.

The cell tissue sheet 51 is therefore provided with a larger thickness, and as a result the physical strength of the cell tissue sheet 51 increases. Hence, the handling of the cell tissue sheet 51 is significantly improved. For example, the thick cell tissue sheet 51 becomes difficult to break in transit for transplantation of the cell tissue sheet 51 into the living body for the purpose of regenerative therapies or the like.

Further, the electrode layer 30 formed on the pore film 70 exerts advantageous effects of effective supply of nutrients and oxygen, effective application of suitable electrical potentials, and the like on the production of cell tissue sheets 51, but not limited thereto. The electrode layer 30 also exerts the same effects on the production of other cell tissues and dispersed individual cells 50.

Figure 8:
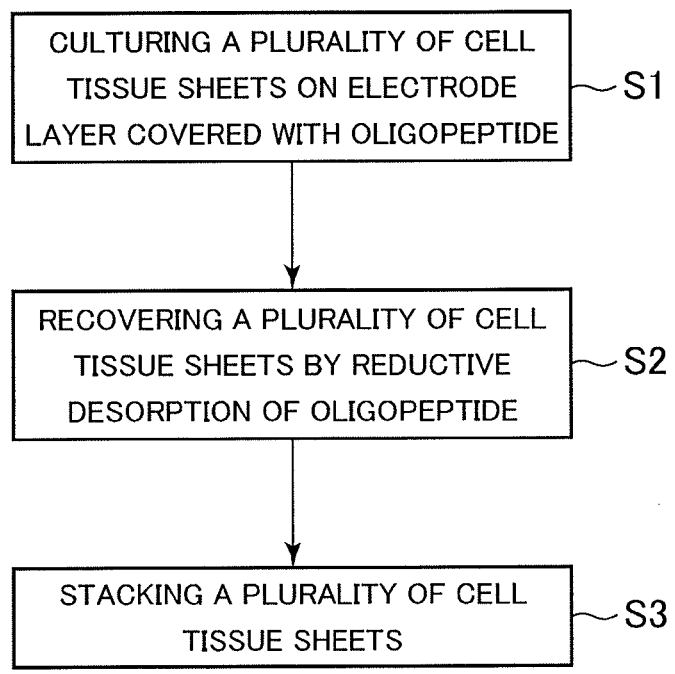
FIG. 8 is an explanatory diagram illustrating a principal step included in another example of a culture method according to the embodiment of this invention.

In the case of the production of the cell tissue sheet 51, as illustrated in FIG. 8, the method of this invention may further include a third step of forming a laminate of the cell tissue sheets 51 detached from the electrode layer 30 (hereinafter referred to as "cell tissue laminate") by stacking a plurality of cell tissue sheets 51 detached from the electrode layer 30 one on top of the other (hereinafter referred to as "stacking step S3").

In this case, specifically, in the culture step S1, a plurality of cell tissue sheets 51 are adhered onto the electrode layer 30 covered with the adhesive oligopeptide 10 and then cultured. Next, in the detachment step S2, the adhesive oligopeptide 10 is subjected to reductive desorption to detach and recover the plurality of the cell tissue sheets 51 from the electrode layer 30. Subsequently, in the stacking step S3, the recovered plurality of cell tissue sheets 51 are stacked to form a sheet-shaped cell tissue laminate. Here, for example, the formation of a plurality of cell tissue sheets 51 may be carried out using a plurality of electrode layers 30 separately formed and placed apart from one another.

In the stacking step S3, a plurality of cell tissue sheets 51 may be cultured in a stacked state for a predetermined time period. In this case, as the culture time passes, the cells 50 of the plurality of cell tissue sheets 51 adhere to one another to unify the plurality of cell tissue sheets 51. As a result, a thicker cell tissue laminate is formed.

The thickness of the cell tissue laminate may be adjusted by the respective thicknesses of the plurality of cell tissue sheets 51 used for the formation of such a cell tissue laminate, and the number of the stacking cell tissue sheets 51. Here, the thickness of each cell tissue sheet 51 may be adjusted, for example, using the above-mentioned porous film 70.

According to the method of this invention including the stacking step S3, therefore, the cell tissue laminate with a desired thickness is reliably produced in an efficient manner. Like the above-mentioned individual cell tissue sheets 51, the cell tissue laminate thus produced is preferably used in a graft to be transplanted into the living body for the purpose of regenerative therapy or the like, and in various other applications.

Next, specific Examples according to this embodiment will be described.

Example 1

Monitoring of Spontaneous Binding and Reductive Desorption of Oligopeptide

Adhesive oligopeptide 10 and nonadhesive oligopeptide 20 illustrated in FIG. 2 and FIG. 3 were designed and prepared. That is, the adhesive oligopeptide 10 was one having an amino acid sequence represented by SEQ ID NO. 1 in which, from the N-terminal to the C-terminal thereof, an intermediate sequence 12 in which a cysteine (C) and three glycines (G) were connected to each other; an alternating sequence 13 in which four lysines (K) and three glutamic acids (E) were alternately connected to each other one by one; and a cell adhesive sequence 14 in which a glycine (G), an arginine (R), a glycine (G), an aspartic acid (D), a serine (S), and a proline (P) were connected to one another in this order, were linked to one another in this order.

Further, the nonadhesive oligopeptide 20 was one having an amino acid sequence represented by SEQ ID NO. 2 in which, from the N-terminal to the C-terminal thereof, an intermediate sequence 22 in which a cysteine (C) and three glycines (G) were connected to each other, and an alternating sequence 23 in which four lysines (K) and three glutamic acids (E) were alternately connected to each other one by one, were linked to one another in this order. In other words, the amino acid sequence of the nonadhesive oligopeptide 20 was the same as that of the above-mentioned adhesive oligopeptide 10 except that the former did not have the cell adhesive sequence 14. These adhesive oligopeptide 10 and nonadhesive oligopeptide 20 were prepared using the custom peptide synthesis service provided by Sigma-Aldrich Corporation.

Using a quartz crystal microbalance (QCM) apparatus (QCA 922, manufactured by SEIKO EG&G), the adhesive oligopeptide 10 was chemically adsorbed on the surface of a crystal resonator (QA-A9M-AU, manufactured by SEIKO EG&G) on which a gold thin film of 5 mm in diameter (equivalent to the electrode layer 30) was formed. A mass change generated in this chemical adsorption process was then measured as a resonance frequency change.

In other words, first, 500 µL of pure water was placed in a chamber (QA-CL4, manufactured by SEIKO EG&G), on which the crystal resonator was fixed, to stabilize resonance frequency. Next, 2 µL of an aqueous oligopeptide solution containing 1 mM of the adhesive oligopeptide 10 was gently introduced into the chamber. Subsequently, resonance frequency changes of the crystal resonator were continuously monitored.

Figure 9:
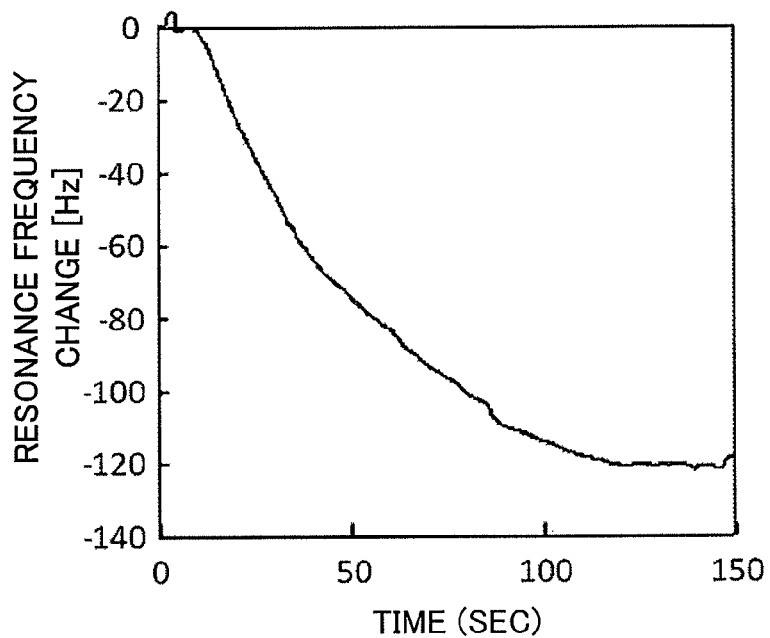
FIG. 9 is an explanatory diagram showing an example of a result of evaluation on chemical adsorption of an oligopeptide on an electrode layer in an Example according to the embodiment of this invention.

FIG. 9 shows the measurement results. In FIG. 9, the horizontal axis represents a time (second) passed from the introduction of the aqueous oligopeptide solution into the chamber, and the vertical axis represents the measured resonance frequency change (Hz). As illustrated in FIG. 9, the spontaneous binding of the adhesive oligopeptide 10 onto the surface of gold was saturated by about 150 seconds and a frequency change of about 120 Hz was observed.

Because the QCM apparatus used had a sensitivity of 0.38 ng per Hz, the adhesive oligopeptide 10 molecules exhibited a chemical adsorption of about 233 ng per unit area (1 mm$^2$) in view of the gold having a surface area of 19.6 mm$^2$.

Then, the crystal resonator that allowed the adhesive oligopeptide 10 to spontaneously bind as described above was washed with pure water. Subsequently, a three-electrode system was constructed in an aqueous 0.5 M KOH solution such that the crystal resonator modified by the adhesive oligopeptide 10 was provided as the working electrode, a platinum plate was provided as the counter electrode, and a silver/silver chloride (internal solution: saturated NaCl) electrode was provided as the reference electrode.

Then, an electrochemical measurement apparatus (QCM 922, manufactured by SEIKO EG&G) having such a three-electrode system was used to apply an electrical potential to the working electrode and monitor a resonance frequency from the working electrode under the conditions of: a starting voltage of −0.3 V; a minimum sweep voltage of −1.0 V; and a sweep rate of 20 mV/sec.

Figure 10:
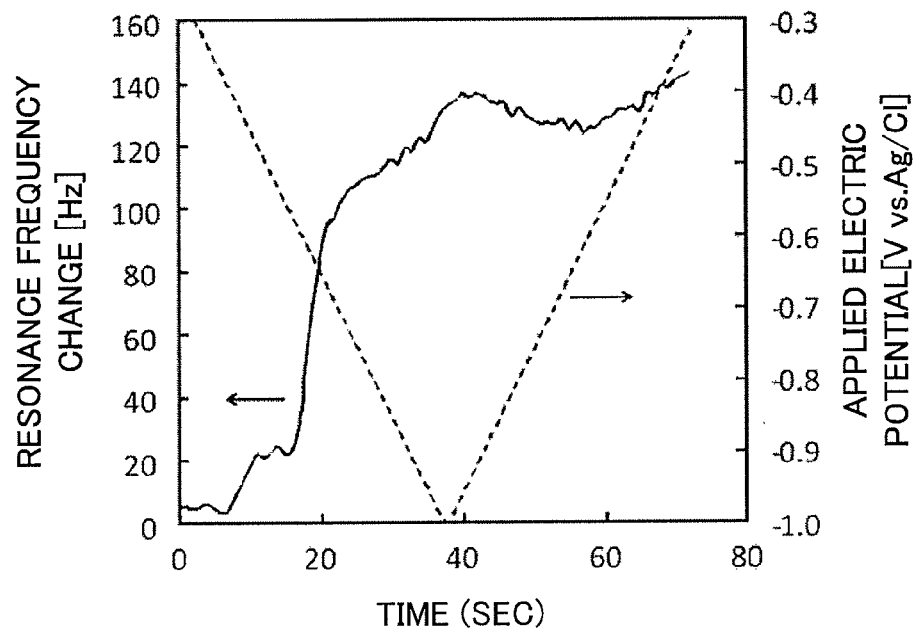
FIG. 10 is an explanatory diagram showing an example of a result of evaluation on desorption of an oligopeptide from an electrode layer through application of an electrical potential in an Example according to the embodiment of this invention.

FIG. 10 shows the measurement results. In FIG. 10, the horizontal axis represents a time (seconds) from starting electrical potential application, the right vertical axis represents an applied voltage (V vs. Ag/Cl), and the left axis represents a resonance frequency change (Hz).

As shown in FIG. 10, in electrical potential scanning from −0.3 V to −1.0 V in a negative direction, an increase in resonance frequency from an electrical potential application of −0.6 V, i.e., desorption of the adhesive oligopeptide 10, was observed. In contrast, in electrical potential scanning from −1.0 V to −0.3 V in a positive direction, no significant change in resonance frequency was observed. In other words, it was observed that the application of an electrical potential at about −0.6 V caused desorption of the adhesive oligopeptide 10 from the surface of gold, and the accompanied frequency change was about 110 Hz.

Because the QCM apparatus had a sensitivity of 0.38 ng per Hz, the adhesive oligopeptide 10 molecules exhibited a chemical adsorption of about 213 ng per unit area (1 mm$^2$) in view of the gold having a surface area of 19.6 mm$^2$. From a comparison between FIG. 9 and FIG. 10, it was observed that, among the adsorbed adhesive oligopeptide 10 molecules, 90% or more of them were desorbed by electrical potential application.

[Measurement of Amount of Protein Nonspecifically Adsorbed on Oligopeptide-Modified Surface]

Using a QCM apparatus (AFFINIX QN, manufactured by Initium Co., Ltd.), the adhesive oligopeptide 10 was chemically adsorbed on the surface of a crystal resonator (manufactured by Initium Co., Ltd.) on which a gold thin film of 1.2 mm in diameter was formed. An amount of protein adsorbed on the surface of the crystal resonator was measured. The proteins used were fibronectin (manufactured by SIGMA) and serum-albumin (manufactured by SIGMA).

First, an aqueous oligopeptide solution containing 1 mM of adhesive oligopeptide 10 was dropped onto the surface of gold (equivalent to the electrode layer 30) of the crystal resonator to chemically adsorb thereon. After one hour, the surface of the crystal resonator was washed with pure water and then dried. The dried crystal resonator was mounted on the QCM apparatus, and the measurement was then started. The resonance frequency was stabilized by waiting until the resonance frequency reached about ±3 Hz per minute (5 to 15 minutes). The stabilized resonance frequency was defined as a resonance frequency before protein adsorption.

Next, the crystal resonator was temporarily detached from the QCM apparatus. Then, an aqueous fibronectin solution prepared by dissolving 0.1 mM fibronectin in PBs or an aqueous serum-albumin solution prepared by dissolving a 0.1 mM serum solution in PBS was dropped onto the surface of gold of the crystal resonator. After 30 minutes, the surface of gold of the crystal resonator was washed with PBS and dried. The crystal resonator was mounted on the QCM apparatus again and then stabilized, and a resonance frequency at this time was read. The stabilized resonance frequency was defined as a resonance frequency after protein adsorption.

The resonance frequency change before and after protein adsorption was obtained from a difference between the resonance frequency before the protein adsorption and the resonance frequency after the protein adsorption. Because the QCM apparatus used had a sensitivity of 0.03 ng per Hz, this value was used in calculation of the amount of adsorbed protein.

Figure 11:
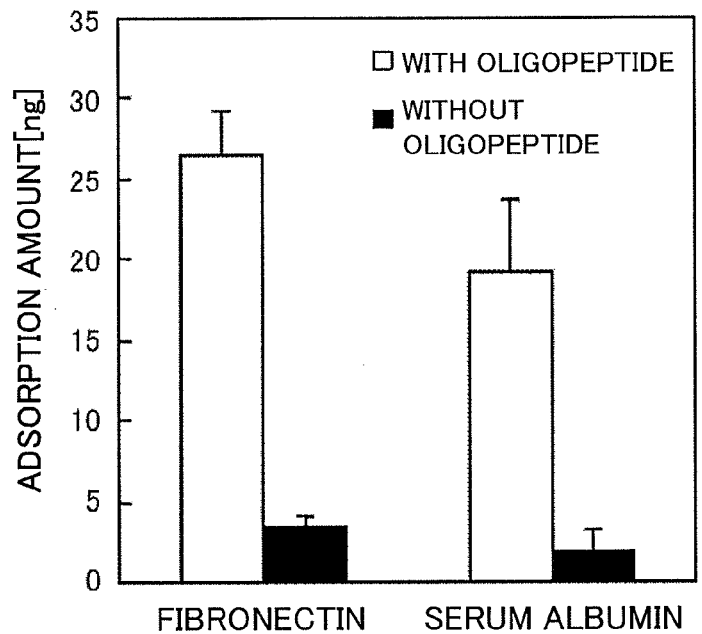
FIG. 11 is an explanatory diagram showing an example of a result of evaluation on adsorption of a protein on the electrode layer coated with an oligopeptide in an Example according to the embodiment of this invention.

FIG. 11 shows the calculation results of the amount of adsorbed protein. In FIG. 11, the horizontal axis represents the kind of used protein (fibronectin or serum-albumin) and the vertical axis represents the amount of the protein adsorbed (ng) on the surface of gold of the crystal resonator. In FIG. 11, further, the white bar represents the result obtained using the crystal resonator without binding of the adhesive oligopeptide 10, and the black bar represents the result obtained using the crystal resonator with binding of the adhesive oligopeptide 10.

As shown in FIG. 11, when the adhesive oligopeptide 10 was bound on the surface of gold of the crystal resonator, the adsorption of fibronectin was inhibited to 13% and the adsorption of serum-albumin was inhibited to 11% in comparison with the case without binding of the adhesive oligopeptide. In other words, it was observed that the adhesive oligopeptide 10 significantly suppressed the adsorption of protein.

[Measurement of Peak Electrical Potential for Reductive Desorption]

As the substrate for forming the electrode layer 30, a flat heat resistant glass substrate (3 inches in diameter and 500 μm in thickness, manufactured by Corning Co., Ltd.) was used. An aqueous solution prepared by mixing 25% aqueous ammonia, 30% hydrogen peroxide, and pure water at a volume ratio of 1:1:4 was boiled. The glass substrate was then soaked in the boiling aqueous solution. Subsequently, the glass substrate was rinsed with pure boiling water and then naturally dried.

Subsequently, a chromium thin film of about 4 nm in thickness was prepared by sputtering chromium for 2 minutes on the surface of a glass substrate using a sputter deposition apparatus (CFS-4ES, manufactured by Shibaura Mechatronics Co., Ltd.) under the conditions of an output of 100 W and an argon atmosphere of 0.3 Pa. Under the same conditions, further, gold was sputtered for 2 minutes on the chromium thin film of the glass substrate to form a gold film (equivalent to the electrode layer 30) of about 4 nm in thickness. The glass substrate on which the gold film was formed was cut into a rectangle flat plate of 10 mm×10 mm in size using a dicing saw (A-WD-10A, manufactured by Tokyo Seimitsu Co., Ltd.). Subsequently, the rectangle flat plate was washed with pure water and naturally dried.

The electrode substrate prepared as described above was soaked overnight in an aqueous oligopeptide solution containing 1.0 μM of the nonadhesive oligopeptide 20. The electrode substrate was then washed with pure water. Consequently, the electrode substrate having the gold thin film surface on which the nonadhesive oligopeptide 20 was bound was obtained.

A three-electrode system was constructed in an aqueous 0.5 M KOH solution such that the electrode substrate, on which the nonadhesive oligopeptide 20 was bound, was provided as the working electrode, a platinum plate was provided as the counter electrode, and a silver/silver chloride (internal solution: saturated KCl) electrode was provided as the reference electrode. Then, an electrochemical measurement apparatus (AUTOLAB, manufactured by Metrohm Autolab, The Netherlands) having such a three-electrode system was used to apply an electrical potential to the working electrode and monitor a current value passing through the working electrode under the conditions of: a starting voltage of −0.3 V; a minimum sweep voltage of −1.0 V; and a sweep rate of 20 mV/sec.

Figure 12:
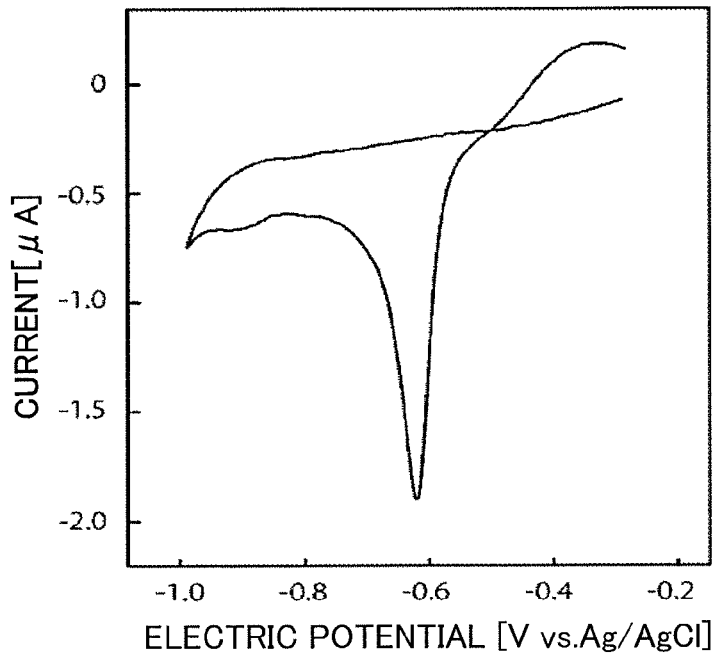
FIG. 12 is an explanatory diagram showing an example of a cyclic voltammogram obtained through application of an electrical potential onto the electrode layer coated with an oligopeptide in an Example according to the embodiment of this invention.

FIG. 12 shows a cyclic voltammogram obtained by a sweep of one cycle. In FIG. 12, the horizontal axis represents an applied electrical potential (V vs. Ag/AgCl) and the vertical axis represents a measured current value (μA).

As shown in FIG. 12, a comparatively broad current peak was observed in the vicinity of −0.6 V in a sweeping (scanning) electrical potential range of −0.3 V to −1.0 V. It is thought that this peak may be a result of detecting a reduction current as a peak because a negative electrical potential of −0.6 V was applied to the surface of the working electrode and caused reduction of the nonadhesive oligopeptide 20 bound to the surface of the working electrode and detachment of the nonadhesive oligopeptide 20 from the surface thereof. Thus, the peak electrical potential for reductive desorption of the nonadhesive oligopeptide 20 was determined as −0.6 V. It was also predicted that reductive desorption of the adhesive oligopeptide 10 occurred through application of the same degree of electrical potential as that of the nonadhesive oligopeptide 20 because the amino acid sequence of the adhesive oligopeptide 10 was the same as the amino acid sequence of the nonadhesive oligopeptide 20 except that the former had the cell adhesive sequence 14.

From the above-mentioned results, for the purpose of reductive desorption of the adhesive oligopeptide 10 and the nonadhesive oligopeptide 20, which were bound to the electrode layer 30 made of a gold thin film, from the electrode layer 30, the application of an electrical potential (e.g., −1.0 V) negatively larger than −0.6 V to the electrode layer 30 was considered as effective.

[Preparation of Electrode for Testing Cell Detachment]

Like the measurement of reductive desorption peak as described above, an electrode substrate formed of a glass substrate on which a gold thin film was formed was soaked overnight in an aqueous oligopeptide solution containing 5 μM of the adhesive oligopeptide 10 and 45 μM of the nonadhesive oligopeptide 20. The electrode substrate was then washed with pure water. Consequently, the electrode substrate having a gold thin film surface on which the adhesive oligopeptide 10 and the nonadhesive oligopeptide 20 were bound at a mole ratio of 1:9 (hereinafter referred to as "10% adhesive electrode") was obtained. Similarly, further, an aqueous oligopeptide solution containing 50 μM of the adhesive oligopeptide 10 only was used to obtain an electrode substrate having a gold thin film surface on which only the adhesive oligopeptide 10 was bound (hereinafter referred to as "100% adhesive electrode").

Also, as a control of the comparison, an adhesive alkanethiol generated by a binding reaction between Dithiobis (succinimidyl undecanoate) and a cell adhesive RGD peptide (manufactured by Peptide Institute Inc.) formed of a glycine-arginine-glycine-aspartic acid-serine sequence was prepared and subjected to the same procedures as those described above to obtain an electrode substrate having a gold thin film surface on which the adhesive alkanethiol was bound (hereinafter referred to as "alkanethiol electrode"). Further, an electrode substrate having a gold thin film surface on which none of the adhesive oligopeptide 10, the nonadhesive oligopeptide 20, and the adhesive alkanethiol was formed (hereinafter referred to as a "gold electrode") was also prepared. Consequently, four different electrode substrates, the 10% adhesive electrode, the 100% adhesive electrode, the alkanethiol electrode and the gold electrode were prepared.

[Preparation of Cells]

Cells used were 3T3 fibroblasts (purchased from Riken Institute of Physical and Chemical Research). A culture medium used was one prepared by adding 10% fetal bovine serum (FBS) to DMEM (manufactured by Cambrex).

The cells were precultured for three days in a 100-mmm diameter polystylene dish (BD Falcon, manufactured by Japan Becton Dickinson and Company) containing 12 mL of the culture medium to grow the cells. After the growth, the cells were recovered by trypsin treatment.

[Adherence and Culture of Cells]

The cells precultured as described above were suspended in the culture medium at a density of $2.5\times10^5$ cells/mL to prepare a cell dispersion solution. Subsequently, 2 mL of the cell dispersion solution were placed in a 35-mm diameter dish provided with any one of the four different electrode substrates prepared as described above. In other words, the cells were seeded at a density of $5\times10^5$ cells/dish. Then, the cells were cultured on the electrode surface for 24 hours at a temperature of 37° C. under an atmosphere of 5% carbon dioxide/95% air saturated with water vapor.

[Detachment of Cells by Electrical Potential Application]

A three-electrode system was constructed such that an electrode on which the cells cultured as described above were adhered was provided as the working electrode, a platinum plate was provided as the counter electrode, and a silver/silver chloride (inner solution: saturated KCl) electrode was provided as the reference electrode.

The electrode substrate provided as the working electrode was horizontally fixed on the bottom surface of a 35-mm diameter polystyrene dish (BD Falcon, manufactured by Japan Becton Dickinson and Company) and soaked in a phosphate buffer solution. In addition to the working electrode, further, the counter electrode and the reference electrode were also soaked in the phosphate buffer solution in the dish.

As the electrical potential-applying portion, a potentiostat (manufactured by Flokuto Denko Co., Ltd.) was used. Then, the potentiostat was used to continuously apply a constant electrical potential of $-1.0$ V, which was 0.4 V more negative than a peak electrical potential ($-0.6$ V) for reductive desorption of the nonadhesive oligopeptide 20, to the working electrode.

Subsequently, at each of time points of immediately after starting the electrical potential application and 1, 2, and 3 minutes after starting the electrical potential application, the number of cells adhered onto the electrode surface of the working electrode was counted under a phase contrast microscope. Evaluation was then performed on a proportion (%) of the number of cells adhered onto the electrode surface at each time of electrical potential application to the number of cells adhered onto the electrode surface immediately after the electrical potential application, which was taken as 100%.

Figure 13:
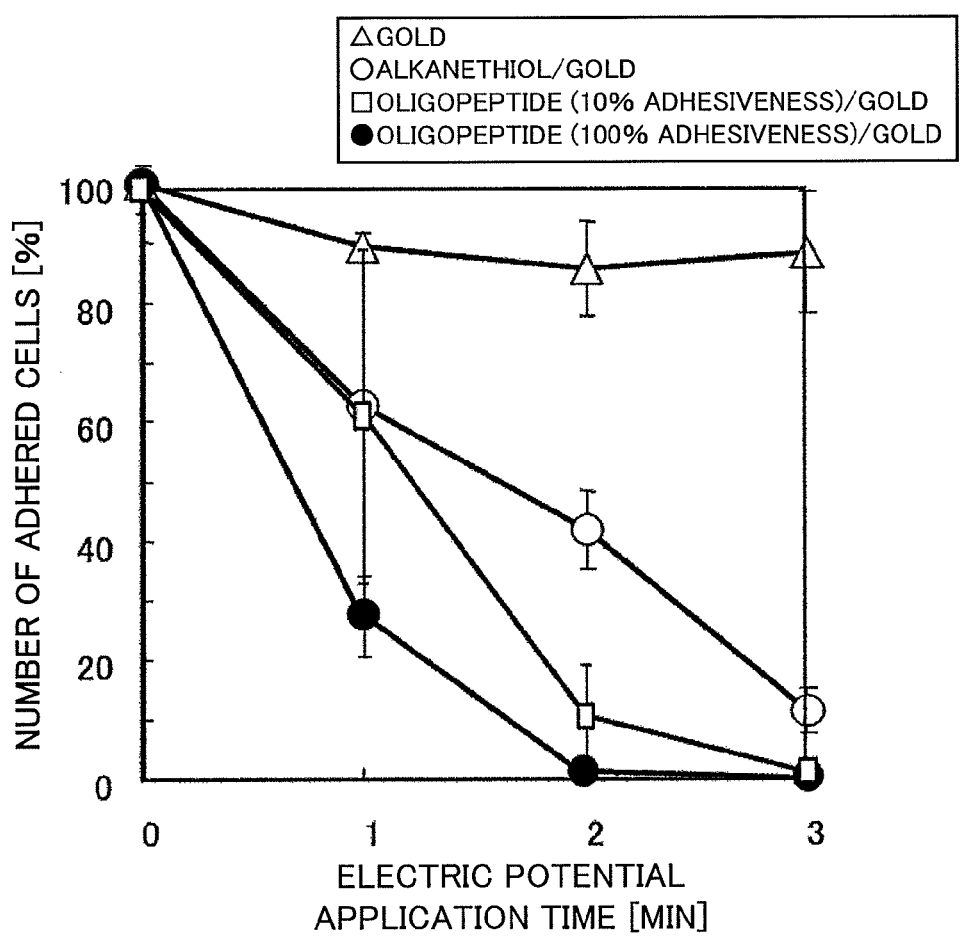
FIG. 13 is an explanatory diagram showing an example of a result of evaluation on the number of cells detached from the electrode layer through application of an electrical potential in an Example according to the embodiment of this invention.

FIG. 13 shows the evaluation results. In FIG. 13, the horizontal axis represents a time (min.) passed after starting the electrical potential application and the vertical axis represents the proportion (%) of the number of cells adhered onto the electrode surface at each time of the electrical potential application. A black circle mark represents a result when using the 100% adhesive electrode ("oligopeptide (100% adhesive)/gold"), a white square mark represents a result when using the 10% adhesive electrode ("oligopeptide (10% adhesive)/gold"), a white circle mark represents a result when using the alkanethiol electrode ("alkanethiol/gold"), and a white triangular mark represents a result when using the gold electrode ("gold").

As shown in FIG. 13, when the cells were directly adhered onto the electrode surface formed of a gold thin film (i.e., when the gold electrode was used), most of the cells were not detached by the electrical potential application. On the other hand, when the cells were adhered via the adhesive oligopeptide 10 or the adhesive alkanethiol (i.e., when the 10% adhesive electrode, 100% adhesive electrode, or alkanethiol electrode was used), it was observed that the cells were detached by the electrical potential application.

In the case of using the alkanethiol electrode, however, about 45% of the cells remained without being detached at a time of 2 minutes from the start of the electrical potential application. In contrast, in the case of using the adhesive oligopeptide 10, the cells were detached more quickly than in the case of using the adhesive alkanethiol. In other words, after 2 minutes from the start of the electrical potential application, most of the cells adhered onto the surface of the 10% adhesive electrode and the 100% adhesive electrode were detached and suspended in the phosphate buffer solution. Further, the number of cells remaining after 3 minutes was substantially zero percent. In particular, in the case of using the 100% adhesive electrode, an extremely quick detachment of the cells was achieved.

Thus, it was confirmed that, by allowing the cells to adhere to the electrode surface via the adhesive oligopeptide 10, the electrical potential application allowed the cells to be detached more reliably and more efficiently from the surface thereof compared with the conventional case.

Example 2

Preparation of Electrode for Testing Cell Tissue Sheet Detachment

In a manner similar to the above-mentioned Example 1, an electrode substrate formed of a glass substrate on which a gold thin film was formed was soaked overnight in an aqueous oligopeptide solution containing 1.0 µM of the adhesive oligopeptide 10. Thus, the electrode substrate having a gold thin film surface on which the adhesive oligopeptide 10 was bound (equivalent to the electrode layer 30) was prepared.

[Adherence and Culture of Cells]

3T3 fibroblasts (purchased from Riken Institute of Physical and Chemical Research) were suspended in the culture medium at a density of $5.0\times10^5$ cells/mL to prepare a cell dispersion solution. Subsequently, 2 mL of the cell dispersion solution were placed in a 35-mm diameter dish including the electrode substrate. The cells were cultured for one week under the same conditions as those of the above-mentioned Example 1 except for the seeding density of the cells.

Consequently, at the time of 48 hours from the start of the culture, the cells were adhered onto the electrode surface while forming two-dimensional binding with one another to form a sheet-shaped cell tissue. In other words, a cell tissue sheet adhered onto the electrode surface was formed.

[Detachment of Cell Tissue Sheet by Electrical Potential Application]

In a manner similar to the above-mentioned Example 1, a three-electrode system including a working electrode formed of an electrode substrate on which the adhesive oligopeptide 10 and the nonadhesive oligopeptide 20 were bound was prepared. Then a potentiostat was used to continuously apply a constant electrical potential of $-1.0$ V to the working electrode in a phosphate buffer solution. As a result, at the time of 5 minutes from the start of the electrical potential application, the entire cell tissue sheet was detached from the electrode surface and suspended in the phosphate buffer solution.

In other words, the continuous application of the constant electrical potential on the working electrode on which the cell tissue sheet was adhered allowed the cell tissue sheet to be detached from the electrode surface of the working electrode while keeping its sheet shape.

Further, to confirm the survival state of cells included in the cell tissue sheet peeled from the electrode surface, the recovered cell tissue sheet was soaked for 5 minutes in a phosphate buffer solution containing fluorescein diacetate (FDA, manufactured by Wako Pure Chemical Industries, Ltd.) of 10

μg/mL in concentration and ethidium bromide (EB, manufactured by Wako Pure Chemical Industries, Ltd.) of 40 μg/mL in concentration.

Thus, living cells and dead cells in the cell tissue sheet were fluorescently-stained with FDA and EB, respectively, in a selective manner. As a result, it was confirmed that most cells in the recovered cell tissue sheet survived.

According to the method of this invention, therefore, the cell tissue sheet cultured on the electrode surface is reliably, noninvasively detached and recovered in an efficient manner. In other words, it was confirmed that the method of this invention was extremely useful as a method of manufacturing a cell tissue sheet.

Example 3

Preparation of Culture Device Having Electrode Layer Formed on Porous Film

Figure 14:
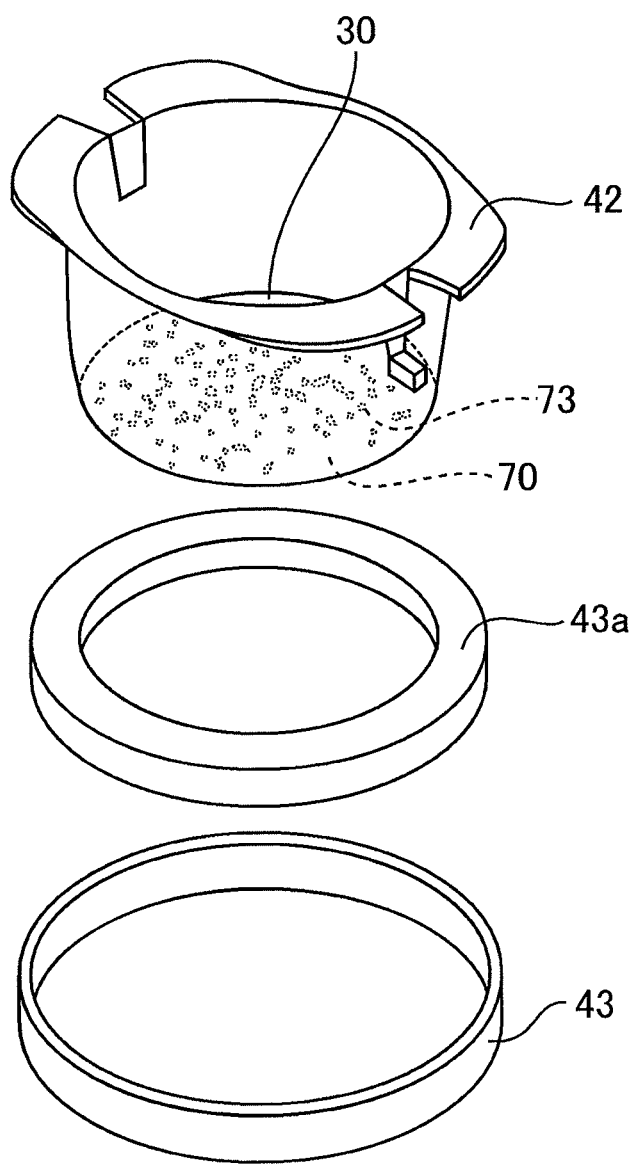
FIG. 14 is an explanatory diagram showing an example of a culture vessel containing a porous film, which is used in an Example according to the embodiment of this invention.

A cell tissue sheet was manufactured using the electrode layer 30 formed on the porous film 70. In other words, as illustrated in FIG. 14, a culture system as illustrated in FIGS. 7A to 7C was constructed using the first culture vessel 42 having the bottom portion formed of the porous film 70 and the second culture vessel 43 for supporting the first culture vessel 42, so that the porous film 70 was kept in a state of being suspended in a culture medium. Further, in the example illustrated in FIG. 14, the second culture vessel 43 had a silicon ring 43a housed in the second culture vessel 43 while supporting the first culture vessel 42 so as to keep the porous film 70 in a state of being suspended in the culture medium.

Figure 15:
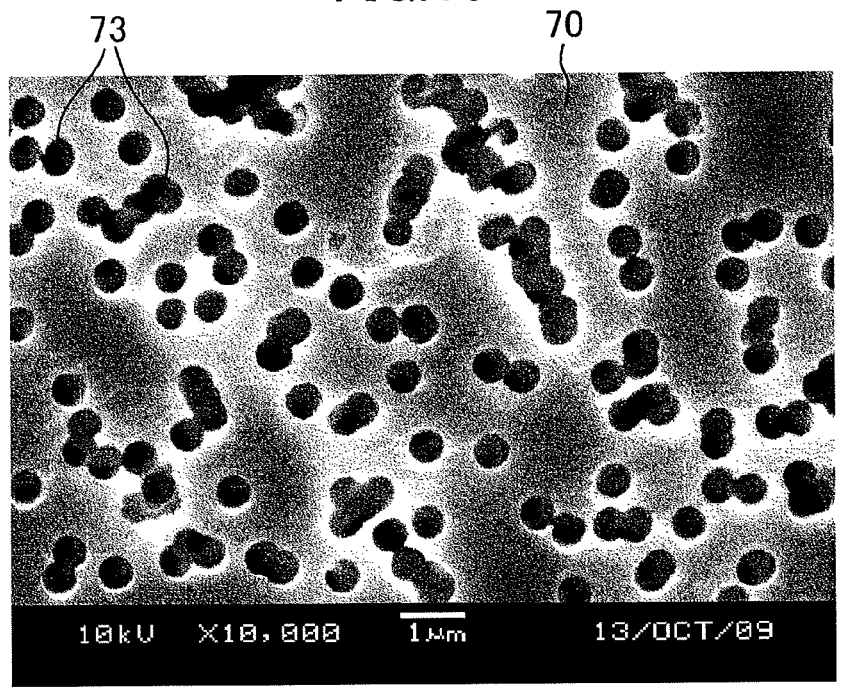
FIG. 15 is an explanatory diagram showing an example of an electron microgram of the porous film used in the Example according to the embodiment of this invention.

The first culture vessel 42 used was a cell insert membrane (Cell Culture Insert #353493, manufactured by BD Falcon™). The first culture vessel 42 had a porous film 70 made of polyethylene terephthalate as its bottom portion. The porous film 70 had a thickness of about 20 to 25 μm and an aperture ratio of about 12.6%, and had a large number of through-holes 73 of about 0.4 μm in diameter. FIG. 15 shows an electron micrograph of the used porous film 70. As illustrated in FIG. 15, the large number of pores 73 were formed in the porous film 70 and penetrated from one surface to the other surface of the porous film 70.

The formation of the electrode layer 30 on the surface of the porous film 70 (i.e., the surface corresponding to the upper surface 71 illustrated in FIG. 6) was performed as follows. A sputter deposition apparatus (CFS-4ES, manufactured by Shibaura Mechatronics Co., Ltd.) was used to sputter chromium for 2 minutes on the surface of the porous film 70 of the insert membrane under the conditions of an output of 100 W and an argon atmosphere of 0.3 Pa. As a result, a chromium thin film of about 4 nm in thickness was formed. Further, under the same conditions, gold was sputtered for 2 minutes on a chromium thin film on a glass substrate to form a gold thin film of about 40 nm in thickness (electrode layer 30). Further, the electrode layer 30 formed on the surface of the porous film 70 was soaked overnight in an aqueous oligopeptide solution containing 1.0 μM of the adhesive oligopeptide 10. Subsequently, the electrode substrate was washed with pure water. Consequently, the electrode substrate formed of the porous film 70 having the electrode layer 30 onto which the adhesive oligopeptide 10 was adhered was obtained.

[Adherence and Culture of Cells]

Precultured 3T3 fibroblast cells were suspended in a culture medium at a density of $5.0 \times 10^5$ cells/mL to prepare a cell dispersion solution. The culture medium used was one prepared by adding 10% fetal bovine serum (FBS) to DMEM (manufactured by Cambrex). Subsequently, 2 mL of the cell dispersion solution were placed on a porous film 70 of an insert membrane prepared as described above. In other words, the cells were seeded at a density of $1 \times 10^6$ cells/insert membrane. Further, 2.5 mL of the culture medium were placed in a second culture vessel 43 supporting a first culture vessel 42. The cells were cultured for two weeks on the electrode surface at a temperature of 37° C. under an atmosphere of 5% carbon dioxide/95% air saturated with water vapor to form a cell tissue sheet.

[Detachment of Cell Tissue Sheet by Electrical Potential Application]

A three-electrode system was constructed such that the porous film 70 having the electrode 30 on which the cell tissue sheet cultured as described above was adhered was provided as the working electrode, a platinum plate was provided as the counter electrode, and a silver/silver chloride (inner solution: saturated NaCl) electrode was provided as the reference electrode. The culture vessel 42 having the working electrode was fixed on the culture vessel 43 and then filled with 5 mL of a phosphate buffer solution. Further, the counter electrode and the reference electrode were also soaked in the phosphate buffer solution in the culture vessel 42. As an electrical potential-applying portion, a potentiostat (manufactured by Hokuto Denko Co., Ltd.) was used. Then, a constant electrical potential of −1.0 V was applied to the working electrode for 5 minutes by the potentiostat. In addition to the voltage application, the culture vessel 42 was pushed into a silicon ring 43a (i.e., downward) to allow a phosphate buffer solution to be supplied from the under surface 72 to the upper surface 71 of the porous film 70 via pores 73. The cell tissue sheet was thereby suspended from the porous film 70 and recovered.

Figure 16A:
FIG. 16A is an explanatory diagram showing an example of a cross-sectional photograph of a cell tissue sheet formed by 7-day culture of cells on an electrode layer formed on the bottom surface of a culture dish in an Example according to the embodiment of this invention.
Figure 16B:
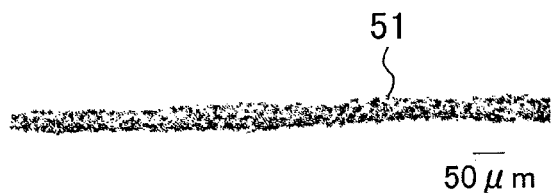
FIG. 16B is an explanatory diagram showing an example of a cross-sectional photograph of a cell tissue sheet formed by 7-day culture of cells on an electrode layer formed on the surface of the porous film in an Example according to the embodiment of this invention.
Figure 16C:
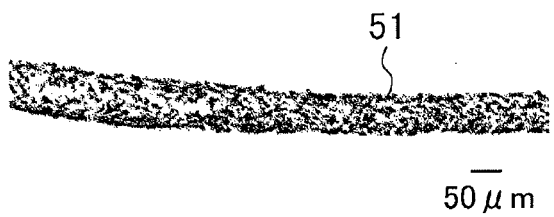
FIG. 16C is an explanatory diagram showing an example of a cross-sectional photograph of a cell tissue sheet formed by 21-day culture of cells on an electrode layer formed on the surface of the porous film in Example according to the embodiment of this invention.

The cross section of the cell tissue sheet 51 detached and recovered from the electrode surface as described above was stained with hematoxylin eosin (HE) and then observed with a phase contrast microscope. FIGS. 16A to 16C illustrate the observation results, respectively. FIG. 16A shows observation results of a cell tissue sheet 51 recovered after culture for 7 days on an electrode surface on the bottom surface of a culture dish. FIG. 16B shows observation results of a cell tissue sheet 51 recovered after culture for 7 days on an electrode surface formed on the surface of a porous film 70. FIG. 16C shows observation results of a cell tissue sheet 51 recovered after culture for 21 days on an electrode surface formed on the surface of a porous film 70.

As shown in FIG. 16A and FIG. 16B, a cell tissue sheet 51 having a significantly large thickness was produced by culturing cells on an electrode surface formed on the surface of a porous film 70 (FIG. 16B), compared with the case where an electrode surface formed on the surface of a non-porous surface (FIG. 16A) was used. Further, as illustrated in FIG. 16C, a cell tissue sheet 51 having a still larger thickness was produced by successively culturing the cells on the electrode surface formed on the surface of the porous film 70.

[Preparation of Cell Tissue Laminate]

On the recovered cell tissue sheet, an additionally recovered second cell tissue sheet was stacked and incubated for 5 minutes at a temperature of 37° C. under an atmosphere of 5% carbon dioxide/95% air saturated with water vapor. Subsequently, an additional third cell tissue sheet was further stacked and incubated in a similar manner to produce a cell tissue laminate.

Figure 17:
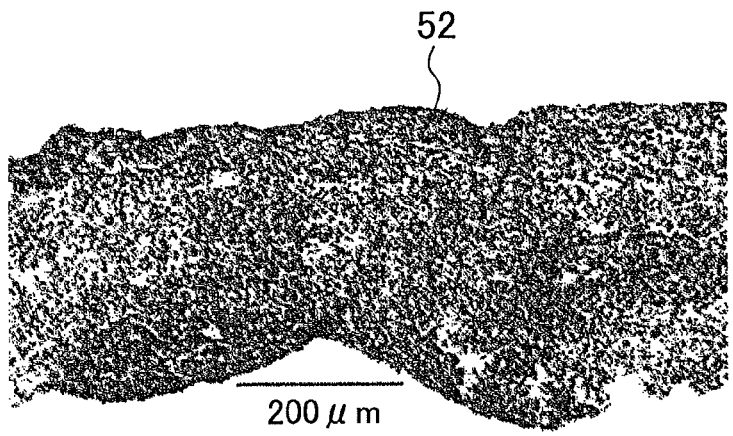
FIG. 17 is an explanatory diagram showing an example of a cross-sectional photograph of a cell tissue laminate formed by stacking a plurality of cell tissue sheets one on top of another in an Example according to the embodiment of this invention.

FIG. 17 shows the results of observation with a phase contrast microscope on the cross section of the cell tissue sheet laminate 52 formed as described above and HE-stained. As illustrated in FIG. 17, since three cell tissue sheets were stacked and unified, a cell tissue sheet laminate 52 having a thickness of 150 to 250 μm was obtained. The cell tissue sheet laminate 52 had sufficient strength to be unbroken, for example, even in the case of being picked and lifted with tweezers.

Example 4

Evaluation on Adherence Ability and Growth Ability of Recovered Cells

An electrode layer 30 on which the adhesive oligopeptide 10 was bound was formed on the surface of the porous film 70 of the insert membrane used in the above-mentioned Example 3. Then, 3T3 fibroblast cells were pre-cultured on the electrode layer 30. A culture medium used was one prepared by adding 10% fetal bovine serum (FBS) to DMEM (manufactured by Cambrex).

A three-electrode system was constructed such that the porous film 70 having the electrode 30, onto which the cultured cell was adhered, was provided as the working electrode, a platinum plate was provided as the counter electrode, and a silver/silver chloride (inner solution:saturated NaCl) electrode was provided as the reference electrode. In a manner similar to the above-mentioned Example 3, a culture vessel 42 having the working electrode was fixed on a culture vessel 43 and then filled with 5 mL of a phosphate buffer solution. Further, the counter electrode and the reference electrode were also soaked in the phosphate buffer solution in the culture vessel 42. As an electrical potential-applying portion, a potentiostat (manufactured by Hokuto Denko Co., Ltd.) was used. Then, a constant electrical potential of −1.0 V was applied to the working electrode for 5 minutes by the potentiostat. As a result, the cells were detached from the electrode layer 30 and then recovered.

Thus, the recovered cells were suspended in the culture medium at a density of $2.85 \times 10^4$ cells/mL to prepare a cell dispersion solution. Subsequently, 2 ml of the cell dispersion solution were placed on the bottom surface of a 35 mm diameter dish made of polystyrene (BD Falcon, manufactured by Japan Becton Dickinson and Company). In other words, cells were seeded at a density of $5.7 \times 10^4$ cells/dish. Then, the cells were cultured for three days at a temperature of 37° C. under an atmosphere of 5% carbon dioxide/95% air saturated with water vapor. During this period, the number of cells was calculated every other day with a phase-contrast microscope.

On the other hand, as a control experiment, 3T3 fibroblast cells were precultured on a polystyrene dish and then recovered by a trypsin treatment. Subsequently, the recovered cells were suspended on the bottom surface of a polystyrene dish under the same conditions as those described above. Then, the number of cells was counted every other day with a phase-contrast microscope.

Figure 18:
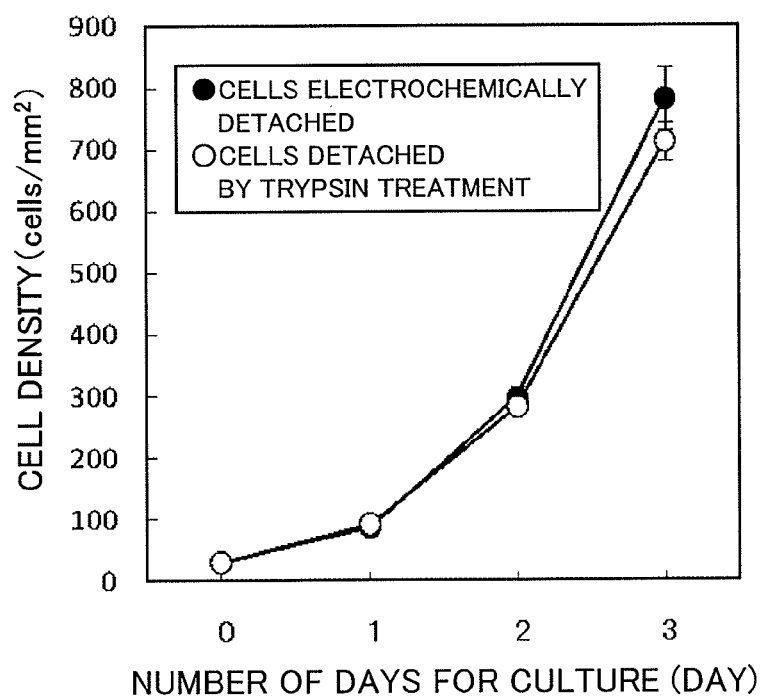
FIG. 18 is an explanatory diagram showing an example of a result of evaluation on growth of cells recovered by being detached from an electrode layer in an Example according to the embodiment of this invention.

FIG. 18 shows the results of counting the number of cells. In FIG. 18, the horizontal axis represents the number of days of the culture (days) and the vertical axis represents the number of cells adhered per $mm^2$ of the bottom surface of the polystyrene dish (cell density (cells/$mm^2$)) in each of the days of the culture. Further, in FIG. 18, a black circle mark represents a result when culturing cells electrochemically detached (due to reductive desorption of adhesive oligopeptide 10) and a white square mark represents a result when culturing cells detached by the trypsin treatment.

As illustrated in FIG. 18, cells recovered from reductive desorption of the adhesive oligopeptide 10 were adhered onto the bottom surface of the polystyrene dish and grown. The growth rate of the cells (doubling time: 15±1.6 hours) was equal to the growth rate of the cells recovered by the trypsin treatment in the control experiment (doubling time: 16±1.5 hours). In other words, it was confirmed that the electrical potential application for reductive desorption of the adhesive oligopeptide 10 did not have any substantial influence on the activities of cells.

Example 5

Preparation of Culture Device Having Electrode Layer Formed on Porous Film

In a manner similar to the above-mentioned Example 3, as illustrated in FIG. 14, a culture system as illustrated in FIGS. 7A to 7C was constructed using a first culture vessel 42 (insert membrane) having a bottom portion formed of a porous film 70 having an electrode 30 on which the adhesive oligopeptide 10 was bound and a second culture vessel 43 supporting the first culture vessel 42 so that the porous film 70 was kept in a state of being suspended in a culture medium.

[Adherence and Culture of Cells]

Cells used were human mesenchymal stem cells (MSCs) useful for regenerative therapies. The MSCs were suspended in the culture medium at a density of $5.0 \times 10^5$ cells/mL to prepare a cell dispersion solution. A culture medium used was one prepared by adding 10% of fetal bovine serum (FBS), 1% of antibiotic/antifungal agent, and 1% of L-glutamine to DMEM (manufactured by Cambrex).

Subsequently, 2 mL of the cell dispersion solution were placed on a porous film 70 of an insert membrane prepared as described above. In other words, the MSCs were seeded at a density of $1 \times 10^6$ cells/insert membrane. Further, 2.5 mL of the culture medium was placed in a second culture vessel 43 supporting a first culture vessel 42. The cells were cultured for four days on the electrode surface at a temperature of 37° C. under an atmosphere of 5% carbon dioxide/95% air saturated with water vapor to form a cell tissue sheet of aggregated MSCs.

[Preparation of Collagen Gel]

As a support of a cell tissue sheet, a collagen gel layer was formed on the cell tissue sheet. Collagen gel was prepared using a collagen solution (Cell matrix Type I-A, manufactured by Nitta Gelatin Inc.). A collagen solution was mixed with a 10-fold concentrated culture medium and a buffer solution at a volume ratio of 8:1:1. The resulting mixture solution was then dropped on a cell tissue sheet and incubated for 30 minutes at a temperature of 37° C. under an atmosphere of 5% carbon dioxide/95% air saturated with water vapor to form a collagen layer on the cell tissue sheet.

[Detachment of Cell Tissue Sheet by Electrical Potential Application]

A three-electrode system was constructed such that the porous film 70 having the electrode 30 onto which the cells cultured as described above was adhered was provided as the working electrode, a platinum plate was provided as the counter electrode, and a silver/silver chloride (inner solution: saturated NaCl) electrode was provided as the reference electrode. The culture vessel 42 having the working electrode was fixed on the culture vessel 43 and then filled with 5 mL of a phosphate buffer solution. Further, the counter electrode and the reference electrode were also soaked in the phosphate buffer solution in the culture vessel 42. As an electrical potential-applying portion, a potentiostat (manufactured by Hokuto Denko Co., Ltd.) was used. Then, a constant electrical potential of −1.0 V was applied to the working electrode for 5 minutes by the potentiostat. In addition to the voltage application, the culture vessel 42 was pushed into a silicon ring 43a to allow a phosphate buffer solution to be supplied from the under surface 72 to the upper surface 71 of the porous film 70 via pores 73. The cell tissue sheet was thereby suspended from the porous film 70 and recovered.

[Evaluation on Survival State of Recovered Cell Tissue Sheet]

A cell tissue sheet detached and recovered from the electrode layer 30 by electrical potential application as described above was stained with fluorescein diacetate (FDA) in a manner similar to the above-mentioned Example 2, and an image thereof was then taken with a fluorescence microscope.

Figure 19:
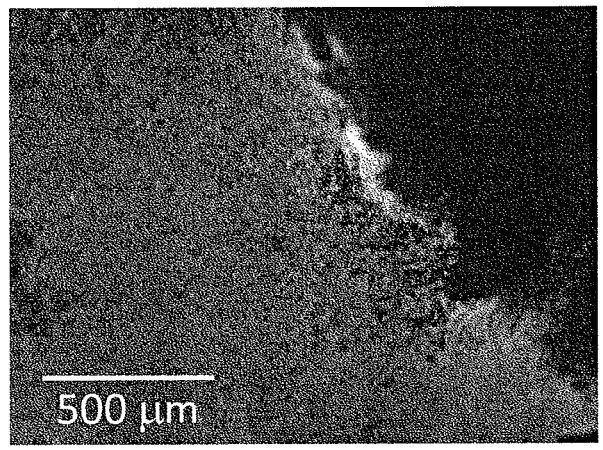
FIG. 19 is an explanatory diagram showing an example of a result of evaluation on a survival state of a cell tissue sheet recovered by being detached from an electrode layer in Example according to the embodiment of this invention.

FIG. 19 shows a photograph of the stained cell tissue sheet taken by the fluorescence microscope. In FIG. 19, a whitened or grayed portion represents the FDA-stained cell tissue sheet, and a black portion represents a background.

As illustrated in FIG. 19, the FDA fluorescently stained throughout the recovered cell tissue sheet. In other words, it was confirmed that cell tissue sheets prepared from MSCs useful in regenerative therapies were efficiently recovered by electrical potential application and MSCs of the cell tissue sheets after the recovery were survived.

REFERENCE SIGNS LIST 10 adhesive oligopeptide, 11 terminal amino acid, 12 intermediate sequence, 13 alternating sequence, 13a acidic amino acid, 13b basic amino acid, 14 cell adhesive sequence, 20 non-adhesive oligopeptide, 21 terminal amino acid, 22 intermediate sequence, 23 alternating sequence, 23a acidic amino acid, 23b basic amino acid, 30 electrode layer, 30a electrical contact portion, 31 reference electrode, 32 counter electrode, 33 electrical potential-applying portion 33, 40 culture portion, 41 substrate, 42 first culture vessel, 43 second culture vessel, 43a ring, 50 cell, 51 cell tissue sheet, 52 cell tissue sheet laminate, 60 culture medium, 70 porous film, 71 upper surface, 72 under surface, 73 pore, 100 oligopeptide layer.

The invention claimed is:

1. A culture method of culturing cells adhered onto an electrode layer, the method comprising:
    a first step of adhering the cells onto the electrode layer and culturing the cells thereon, the electrode layer being coated with an oligopeptide including:
        a terminal amino acid forming one end of the oligopeptide bound to the electrode layer via thiolate;
        a cell adhesive sequence forming another end of the oligopeptide and having a cell-adhesive amino acid sequence; and
        an alternating sequence bound to the one end side of the cell-adhesive sequence, wherein the alternating sequence includes a plurality of acidic amino acids and a plurality of basic amino acids and the acidic amino acids and the basic amino acids alternate one-by-one; and
    a second step of applying, to the electrode layer having the cells adhered thereonto, an electrical potential inducing reductive desorption of the oligopeptide, to thereby detach the cells from the electrode layer.

2. The culture method according to claim 1, wherein the electrode layer is formed on a surface of a porous film held in a state of being suspended in a culture medium.

3. The culture method according to claim 2, wherein:
    in the first step, the cells are adhered onto the electrode and cultured thereon, to thereby form a cell tissue sheet adhered onto the electrode layer; and
    in the second step, an electrical potential inducing reductive desorption of the oligopeptide is applied to the electrode layer having the cell tissue sheet adhered thereonto, to thereby detach the cell tissue sheet from the electrode layer.

4. The culture method according to claim 3, further comprising a third step of stacking a plurality of the cell tissue

---

SEQUENCE LISTING

```
<160> NUMBER OF SEQ ID NOS: 2

<210> SEQ ID NO 1
<211> LENGTH: 17
<212> TYPE: PRT
<213> ORGANISM: Artificial
<220> FEATURE:
<223> OTHER INFORMATION: Synthetic Construct - Oligopeptide with
      Adhesive amino sequence

<400> SEQUENCE: 1

Cys Gly Gly Gly Lys Glu Lys Glu Lys Glu Lys Gly Arg Gly Asp Ser
1               5                   10                  15

Pro

<210> SEQ ID NO 2
<211> LENGTH: 11
<212> TYPE: PRT
<213> ORGANISM: Artificial
<220> FEATURE:
<223> OTHER INFORMATION: Synthetic Construct - Oligopeptide without
      adhesive amino sequence

<400> SEQUENCE: 2

Cys Gly Gly Gly Lys Glu Lys Glu Lys Glu Lys
1               5                   10
``` sheets, each being caused to detach from the electrode layer to thereby form a laminate of the cell tissue sheets.

5. The culture method according to claim 1, wherein:

in the first step, the cells are adhered onto the electrode and cultured thereon, to thereby form a cell tissue sheet adhered onto the electrode layer; and in the second step, an electrical potential inducing reductive desorption of the oligopeptide is applied to the electrode layer having the cell tissue sheet adhered thereonto, to thereby detach the cell tissue sheet from the electrode layer.

6. The culture method according to claim 5, further comprising a third step of stacking a plurality of the cell tissue sheets, each being caused to detach from the electrode layer to thereby form a laminate of the cell tissue sheets.

7. The culture method according to claim 1, wherein the alternating sequence consists of the plurality of acidic amino acids and the plurality of basic amino acids, being alternately bound to each other.

8. The culture method according to claim 1, wherein the electrode layer is coated with a self-assembled monolayer of the oligopeptide.

9. A culture device comprising an electrode layer for adhering cells thereonto and culturing the cells thereon, wherein the electrode layer is coated with an oligopeptide including:

a terminal amino acid forming one end of the oligopeptide bound to the electrode layer via thiolate;

a cell adhesive sequence forming another end of the oligopeptide and having a cell-adhesive amino acid sequence;

an alternating sequence bound to the one end side of the cell-adhesive sequence, wherein the alternating sequence includes a plurality of acidic amino acids and a plurality of basic amino acids and the acidic amino acids and the basic amino acids alternate one-by-one.

10. The culture device according to claim 9, wherein the electrode layer is formed on a surface of a porous film held in a state of being suspended in a culture medium.

11. The culture device according to claim 9, wherein the alternating sequence consists of the plurality of acidic amino acids and the plurality of basic amino acids, being alternately bound to each other.

12. The culture device according to claim 9, wherein the electrode layer is coated with a self-assembled monolayer of the oligopeptide.

* * * * *